(12) United States Patent
Tulla-Puche et al.

(10) Patent No.: US 8,748,388 B2
(45) Date of Patent: Jun. 10, 2014

(54) ANTITUMORAL COMPOUNDS

(75) Inventors: Judit Tulla-Puche, Barcelona (ES); Eleonora Marcucci, Barcelona (ES); Núria Bayó-Puxan, Barcelona (ES); Fernando Albericio, Barcelona (ES); Maria del Carmen Cuevas Marchante, Madrid (ES)

(73) Assignee: Pharma Mar, S.A., Madrid (ES)

(*) Notice: Subject to any disclaimer, the term of this patent is extended or adjusted under 35 U.S.C. 154(b) by 590 days.

(21) Appl. No.: 12/746,957

(22) PCT Filed: Dec. 10, 2008

(86) PCT No.: PCT/EP2008/067189
§ 371 (c)(1),
(2), (4) Date: Jun. 9, 2010

(87) PCT Pub. No.: WO2009/077401
PCT Pub. Date: Jun. 25, 2009

(65) Prior Publication Data
US 2010/0292163 A1 Nov. 18, 2010
US 2011/0207674 A2 Aug. 25, 2011

(51) Int. Cl.
*A61K 31/33* (2006.01)
*A61K 38/12* (2006.01)
*C07D 245/00* (2006.01)
*C07K 7/54* (2006.01)
*A61P 35/00* (2006.01)

(52) U.S. Cl.
USPC ....... 514/19.2; 514/19.3; 514/19.4; 514/19.5; 514/19.6; 514/19.7; 514/19.8; 514/19.9; 514/183; 530/317; 540/460

(58) Field of Classification Search
None
See application file for complete search history.

(56) References Cited

U.S. PATENT DOCUMENTS

| 5,681,813 | A | 10/1997 | Baz |
| 5,849,540 | A | 12/1998 | Baz |
| 6,214,793 | B1 | 4/2001 | Baz |

FOREIGN PATENT DOCUMENTS

| WO | WO 95/27730 | 10/1995 |
| WO | WO 02/49577 | 6/2002 |

OTHER PUBLICATIONS

Jantzen, Modern Pharmaceutics, 1996, 596.*
Spong-Rodriguez. Advanced Drug Delivery Reviews, 2004, 56, 241-74.*
McClendon. Mutation Research, 2007, 623(1-2), pp. 83-97.*
Metabolite:, http://www.encyclopedia.com/doc/1E1-metabolit.html, accessed Jan. 25, 2008, primary source is Columbia Encyclopedia, 2007.*
Bayó-Puxan, N. et al., "Beyond Azathiocoraline: Synthesis of Analogues," International Journal of Peptide Research and Therapeutics, 2007, 13, pp. 295-306.
Bayó-Puxan, N., "Productes naturals com a font de nous fàrmacs: sintesi en face sólida de depsipéptids cíclics i aïllament d'agents antitumorals d'esponges marines," PhD Tesis, 2006, pp. 1-86.
Bayó-Puxan, N. et al., "Oxathiocoraline: Lessons to be Learned from the Synthesis of Complex N-Methylated Depsipeptides," European Journal Organic Chemisry, 2009, pp. 2957-2974.
Bayó-Puxan, N. et al., "Total Solid-Phase Synthesis of the Azathiocoraline Class Symmetric Bicyclic Peptides," Chemistry European Journal, 2006, 12, pp. 9001-9009.
Biswas, T. et al., "A New Scaffold of an Old Protein Fold Ensures Binding to the Bisintercalator Thiocoraline," Journal of Molecular Biology, 2010, 397, pp. 495-507.
Boger, D.L. et al., "Development of a Solution-Phase Synthesis of Minor Groove Binding Bis-Intercalators Based on Triostin A Suitable for Combinatorial Synthesis," Journal Organic Chemistry, 2000, 65, pp. 5996-6000.
Boger, D.L. et al., "Total syntheses of Thiocoraline and BE-22179: Establishment of Relative and Absolute Stereochemistry," Journal of American Chemical Society, 2000, 122, pp. 2956-2957.
Boger, D.L. et al., "Total synthesis of Thiocoraline and BE-22179 and Assesment of Their DNA Binding and Biological Properties," Journal of American Chemical Society, 2001, 123, pp. 561-568.
Brandon, Esther F.A. et al., "In Vitro characterization of the biotransformation of thiocoraline, a novel marine anti-cancer drug," Investigational New Drugs, 2004, 22, pp. 241-251.
Dawson, S. et al., "Bisintercalator natural products with potential therapeutics applications: isolation, structure determination, synthetic and biological studies," Natural Products Report, 2007, 24, pp. 109-126.
Dell, A et al. "Structure Revision of the Antibiotic Echinomycin", Journal of the American Society, 1975, 97(9), 2497-2502.

(Continued)

Primary Examiner — Noble Jarrell
(74) Attorney, Agent, or Firm — Kenneth H. Sonnenfeld; King & Spalding LLP

(57) ABSTRACT

Antitumoral compounds of Formula I, and pharmaceutically acceptable salts, derivatives, tautomers, prodrugs or stereoisomers thereof Formula I

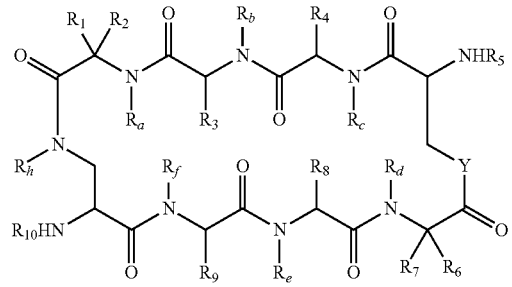

useful as antitumour agents.

23 Claims, No Drawings

(56) References Cited

OTHER PUBLICATIONS

Dietrich, B. et al., "Synthesis of Cyclopeptidic Analogues of Triostin A with Quinoxalines or Nucleobases as Chromophores," European Journal Organic Chemistry, 2005, pp. 147-153.

Erba, E. et al., "Cell cycle perturbations induced by Thiocoraline, a novel antitumor agent," Proceedings of the 88th Annual Meeting of American Association for Cancer Research, AACR; 1997, Apr. 12-16, Abstract No. 688.

Erba, E. et al., "Mode of action of thiocoraline, a natural marine compound with anti-tumour activity," British Journal of Cancer, 1999, 80, pp. 971-980.

Faircloth, G. et al., "Biological activity of thiocoraline. A new depsipeptide from a marine micronospora," Proceedings of the 9th NCI-EORTC-AACR Symposium on New Drugs in Cancer Therapy, 1996, Mar. 12-15, Abstract No. 112.

Lombó, F. et al., "Deciphering the Biosynthesis Pathway of the Antitumor Thiocoraline from a Marine Actinomycete and Its Expression in Two Streptomyces Species," European Journal of Chemical Biology, 2006, 7, pp. 366-376.

Negri, A. et al., "Antitumor Activity, X Ray Crystal Structure, and DNA Binding Properties of Thiocoraline A, a Natural Bisintercalating Thiodepsipeptide," Journal of Medicinal Chemistry, 2007, 50, pp. 3322-3333.

Okada H. et al., "A new topoisornerase II inhibitor, BE-22179, produced by a streptomycete, Producing strain, fermentation, isolation and biological activity," The Journal of Antibiotics, 1994, 47, pp. 129-135.

Romero, F. et al., "Thiocoraline, a New Depsipeptide with Antitumor Activity Produced by a Marine Micromonospora. I. Taxonomy, Fermentation, Isolation, and Biological Activities," Journal of Antibiotics, 1997, 50, pp. 734-737.

Sheoran, A. et al., "Characterization of TioF, a tryptophan 2,3-dioxygenase involved in 3-hydroxyquinaldic acid formation during thiocoraline biosynthesis," Molecular Biosystems, 2008, 4, pp. 622-628.

Shoji, J. et al., "Studies on quinoxaline, antibiotics.III. New Antibiotics, Triostins A, B and C," Journal of Antibiotics, 1961, 14, pp. 335-339.

Sparidans, R.W. et al., "Bioanalysis of thiocoraline, a new marine antitumoral depsipeptide, in plasma by high-performance liquid chromatography and fluorescence detection," Journal of Chromatography B, 1999, 726, pp. 255-260.

Tulla-Puche, J. et al., "Solid-Phase Synthesis of Oxathiocoraline by a Key Intermolecular Disulfide Dimer," Journal of American Chemical Society, 2007, 129, pp. 5322-5323.

Tulla-Puche, J. et al., "NMe Amide as a Synthetic Surrogate for the Thioester Moiety in Thiocoraline," Journal of Medicinal Chemistry, 2009, 52, pp, 834-839.

Yin, J. et al., "Validation and application of a sensitive assay for thiocoraline, a novel marine-derived antineoplastic, in mouse plasma using LC/MS/MS," Proceedings of the 94th Annual Meeting of American Association for Cancer Research, AACR; Jul. 11-14, 2003, Abstract No. 464.

Yin, J. et al., "Validation of a sensitive assay for thiocoraline in mouse plasma using liquid chromatography—tandem massspectrometry," Journal of Chromatography B, 2003, 794, pp. 89-98.

Zolova, O.E et al., "Recent development in Bisintercalator Natural Products," Biopolymers, 2010, 93, pp. 777-790.

Wheate et al., "DNA Intercalators in Cancer Therapy: Organic and Inorganic Drugs and Their Spectroscopic Tools for Analysis," Mini-Reviews in Medicinal Chemistry, 7, pp. 627-648, 2007.

\* cited by examiner

ANTITUMORAL COMPOUNDS

FIELD OF THE INVENTION

The present invention relates to new antitumoral compounds, pharmaceutical compositions containing them and their use as antitumoral agents.

BACKGROUND OF THE INVENTION

In WO 95/27730, Perez Baz et al. disclosed the isolation and the two-dimensional structural elucidation of a new antitumoral agent, Thiocoraline A, from the marine organism *Micromonospora* sp.

They also reported the binding of thiocoraline A, BE-2179 and its analogs to DNA by high-affinity bisintercalation with little or no perceptible sequence selectivity.

Recently, Gago et al. disclosed the X-ray structure of Thiocoraline A and its DNA binding properties (Negri, A.; Marco, E.; Garcia-Hernandez, V.; Domingo, A.; Llamas-Saiz, A. L.; Porto-Sandá, S.; Riguera, R.; Laine, W.; David-Cordonnier, M-H.; Bailly, C.; Garcia-Fernández, L. F.; Vaquero, J. J.; and Gago, F. J. Med. Chem. 2007, 50, 3322-3333).

Thiocoraline A shares several common motifs with a family of antitumoral peptide antibiotics, which includes Triostin A (Shoji, J., et al. J. Antibiot. 1961, 14, 335-339), BE-22179 (Okada, H., et al, J. Antibiot. 1994, 47, 129-135), and Echinomycin (Corbaz, R., et al. Helv. Chim. Acta 1957, 40, 199-204).

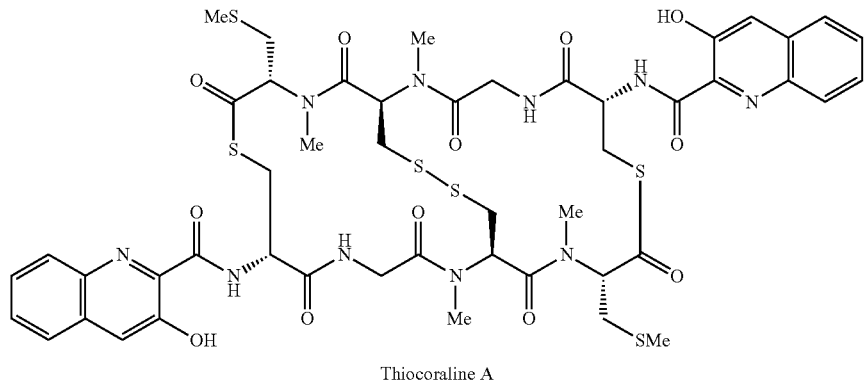

Thiocoraline A

In 1999, Erba et al. reported the activity of this compound as inhibitor of DNA alpha-polimerase at concentrations that inhibit cell cycle progression and clonogenicity (Erba, E.; Bergamaschi, D.; Ronzoni, S.; Faretta, M.; Taverna, S.; Bonfanti, M.; Catapano, C. V.; Faircloth, G.; Jimeno, J.; D'Incalci, M. British J. Cancer 1999, 80, 971-980).

In WO 02/49577, Boger and Lewis disclosed the total synthesis of Thiocoraline A and BE-22179. This total synthesis allowed the elucidation of relative and absolute stereochemistries of Thiocoraline A. They also reported the preparation of Thiocoraline A analogs wherein the 2-hydroxyquinolyl group was replaced with other quinolines or quinoxalines.

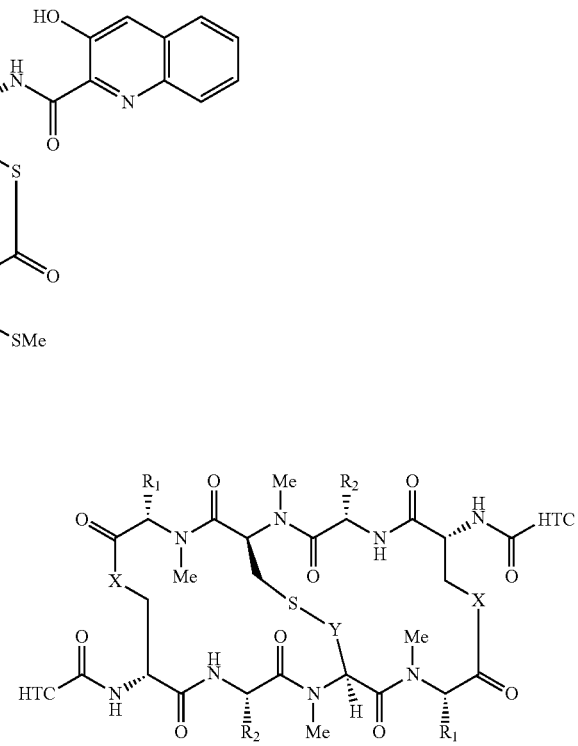

Triostin A: X = O; Y = —SCH$_2$—; R$_1$ = i-Pr; R$_2$ = Me, HTC = 2-quinoxalinyl
BE-22179: X = S; Y = —SCH$_2$—; R$_1$ = CH$_2$=; R$_2$ = H, HTC = 3-hydroxy-2-quinolyl
Echinomycin: X = O; Y = CH(SMe); R$_1$ = i-Pr; R$_2$ = Me; HTC = 2-quinoxalinyl

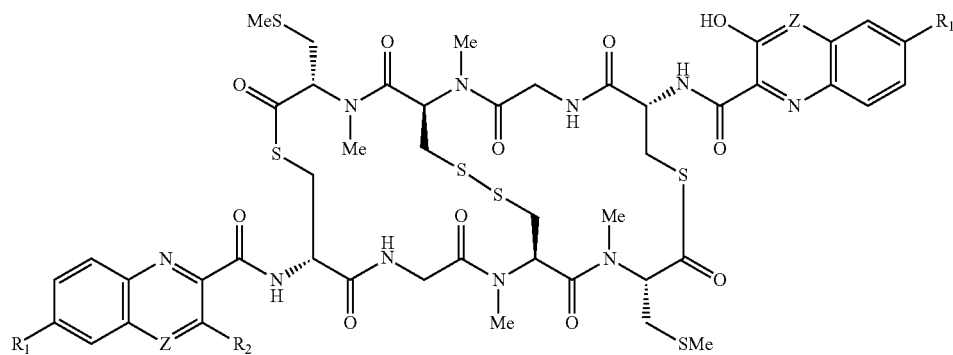

Z = CH, R$_1$ = R$_2$ = H
Z = N, R$_1$ = R$_2$ = H
Z = CH, R$_1$ = OMe, R$_2$ = OH

This group of 2-fold symmetric or pseudosymmetric bicyclic octapeptides shows a complex structure containing: a) a bicyclic structure formed by two peptide chains in an antiparallel mode; b) an ester or thioester linkage at the terminal part of the peptide chain; c) a disulfide or an analogue bridge in the middle of the peptide chains; d) an intercalation chromophore moiety at the N-terminal part; e) the presence of several N-methyl amino acids; and f) non natural amino acid of D configuration.

Boger and Lee reported in 2000 the synthesis and cytotoxic activity against leukemia cell line L1210 of Azatriostin A (Boger, D. L.; Lee, J. K. J. Org. Chem. 2000, 65(19), 5996-6000). Azatriostin A is a Triostin A analogue wherein the ester linkage at the terminal part of the peptide chain has been replaced with an amide linkage. Azatriostin A was two orders of magnitude less active than Triostin A against this cell line.

Other Thiocoraline A analogs disclosed in the prior art are Oxathiocoraline, which shown cytotoxic activity against three cell lines with $GI_{50}$ values between 3.0E-7 M to 4.62E-7 M (Tulla-Puche, J.; Bayó-Puxan, N.; Moreno, J. A.; Francesch, A. M.; Cuevas, C.; Álvarez, M.; and Albericio, F. J. Am. Chem. Soc. 2007, 129, 5322-5323), and Azathiocoraline, which shown cytotoxic activity against a panel of cell lines with $GI_{50}$ values between 5.67E-6 M to 2.58E-7 M (Bayó-Puxan, N.; Fernández, A.; Tulla-Puche J.; Riego, E.; Cuevas, C.; Álvarez, M.; and Albericio, F. Chem. Eur. J. 2006, 12, 9001-9009; Bayó-Puxan, N. Ph. D. Thesis, University of Barcelona, 2006), and Azathiocoraline analogs wherein the intercalation chromophore moeity at the N-terminal part of Thiocoraline A and/or a cyclic amino acid was modified (Bayó-Puxan, N.; Fernández, A.; Tulla-Puche J.; Riego, E.;. Álvarez, M.; and Albericio, F. Int. J. of Peptide Research and Therapeutics. 2007, 13, 295-306).

Compounds [NMe-Leu[4], NMe-Leu[8]] Azathiocoraline, [2QXA, NMe-Ala[4]] Azathiocoraline, and [2QXA, NMe-Ala[4]] Azathiocoraline were also tested against this cell panel with $GI_{50}$ values higher than 9.99 E-6 M (Bayó-Puxan, N. Ph. D. Thesis, University of Barcelona, 2006).

Cancer is a leading cause of death in animals and humans. Huge efforts have been and are still being undertaken in order to obtain an antitumor agents that are active and safe to be administered to patients suffering from a cancer. The problem to be solved by the present invention is to provide compounds that are useful in the treatment of cancer.

SUMMARY OF THE INVENTION

In one aspect, the present invention is directed to a compound of general formula I or a pharmaceutically acceptable salt, derivative, tautomer, prodrug or stereoisomer thereof,

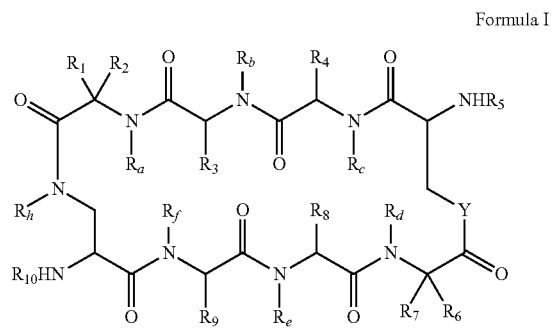

Formula I

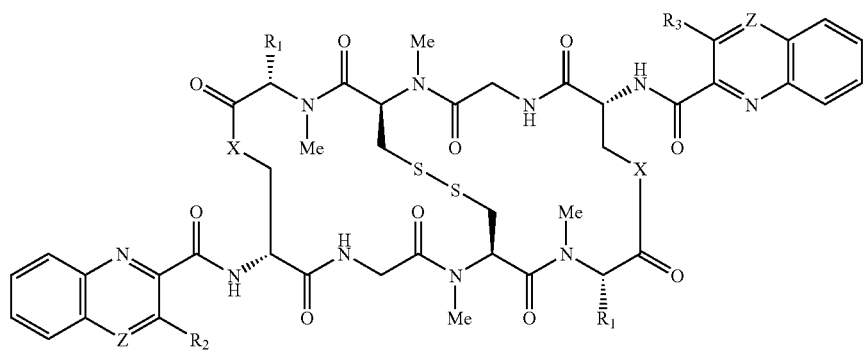

| Compound | X | Z | $R_1$ | $R_2$ | $R_3$ |
|---|---|---|---|---|---|
| Oxathiocoraline | O | CH | —CH$_2$—SMe | OH | OH |
| Azathiocoraline | NH | CH | —CH$_2$—SMe | OH | OH |
| [NMe-Leu[4], NMe-Leu[8]]azathiocoraline | NH | CH | i-Pr | OH | OH |
| Azathiocoraline + 3HQA | NH | CH | —CH$_2$—SMe | OH | (structure shown) |
| [2QXA, NMe-Ala4] Azathiocoraline | NH | N | Me | H | H |
| [2QNA, NMe-Ala4] Azathiocoraline | NH | CH | Me | H | H | wherein $R_1$, $R_4$, $R_6$, and $R_9$ are each independently selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl;

$R_3$ and $R_8$ are each independently a substituted or unsubstituted $C_1$-$C_{12}$ mercaptoalkyl group wherein the mercapto group may be optionally protected; or $R_3$ with $R_8$ form a group —$CH_2$—S—S—$CH_2$—;

$R_2$ is hydrogen;

$R_7$ is hydrogen; or the pair $R_1$-$R_2$ and/or $R_6$-$R_7$ independently form a substituted or unsubstituted $C_1$-$C_{12}$ alkylidene or together with the corresponding C atom to which they are attached form a substituted or unsubstituted $C_3$-$C_{12}$ cycloalkyl;

$R_5$ and $R_{10}$ are each independently selected from amino protecting group and —(C=O)R" wherein each R" is independently selected from substituted or unsubstituted heterocyclic group and substituted or unsubstituted heterocyclylalkyl group;

$R_a$, $R_b$, $R_c$, $R_d$, $R_e$, and $R_f$ are each independently selected from hydrogen and substituted or unsubstituted $C_1$-$C_{12}$ alkyl;

Y is selected from S, O, and $NR_i$;

$R_h$ is selected from substituted or unsubstituted $C_1$-$C_{12}$ alkyl, a —$(CH_2$—$CH_2O)_n$—$CH_3$ group wherein n is from 1 to 25, substituted or unsubstituted $C_2$-$C_{12}$ alkenyl, and substituted or unsubstituted $C_2$-$C_{12}$ alkynyl;

and $R_i$ is a group selected from hydrogen, substituted of unsubstituted $C_1$-$C_{12}$ alkyl, a —$(CH_2$—$CH_2O)_n$—$CH_3$ group wherein n is from 1 to 25, substituted or unsubstituted $C_2$-$C_{12}$ alkenyl, and substituted or unsubstituted $C_2$-$C_{12}$ alkynyl.

In another aspect, the present invention is directed to a compound of formula I or a pharmaceutically acceptable salt, derivative, tautomer, prodrug or stereoisomer thereof for use as a medicament, in particular as a medicament for treating cancer.

In a further aspect, the present invention is also directed to the use of a compound of formula I or a pharmaceutically acceptable salt, derivative, tautomer, prodrug or stereoisomer thereof in the treatment of cancer, or in the preparation of a medicament, preferably for the treatment of cancer. Other aspects of the invention are methods of treatment, and compounds for use in these methods. Therefore, the present invention further provides a method of treating any mammal, notably a human, affected by cancer which comprises administering to the affected individual a therapeutically effective amount of a compound as defined above.

In a yet further aspect, the present invention is also directed to a compound of formula I or pharmaceutically acceptable salt, derivative, tautomer, prodrug or stereoisomer thereof for use as an anticancer agent.

In another aspect, the present invention is directed to pharmaceutical compositions comprising a compound of formula I or a pharmaceutically acceptable salt, derivative, tautomer, prodrug or stereoisomer thereof together with a pharmaceutically acceptable carrier or diluent.

The present invention also relates to a process for obtaining compounds of formula I and the formation of derivatives from these compounds.

DETAILED DESCRIPTION OF PREFERRED EMBODIMENTS

The present invention relates to compounds of general formula I as defined above.

In these compounds the groups can be selected in accordance with the following guidance:

Alkyl groups may be branched or unbranched, and preferably have from 1 to about 12 carbon atoms. One more preferred class of alkyl groups has from 1 to about 6 carbon atoms. Even more preferred are alkyl groups having 1, 2, 3 or 4 carbon atoms. Methyl, ethyl, propyl, isopropyl and butyl, including tert-butyl, sec-butyl and isobutyl are particularly preferred alkyl groups in the compounds of the present invention. Another preferred class of alkyl groups has from 6 to about 10 carbon atoms; and even more preferably 7, 8 or 9 carbon atoms. Heptyl, octyl and nonyl are the most preferred alkyl groups of this class.

Preferred alkenyl and alkynyl groups in the compounds of the present invention may be branched or unbranched, have one or more unsaturated linkages and from 2 to about 12 carbon atoms. One more preferred class of alkenyl and alkynyl groups has from 2 to about 6 carbon atoms. Even more preferred are alkenyl and alkynyl groups having 2, 3 or 4 carbon atoms. Another preferred class of alkenyl and alkynyl groups has from 4 to about 10 carbon atoms, still more preferably 6 to about 10 carbon atoms; and even more preferably 7, 8 or 9 carbon atoms.

Alkylidene groups may be branched or unbranched, and preferably have from 1 to about 12 carbon atoms. One more preferred class of alkylidene groups has from 1 to about 6 carbon atoms. Even more preferred are alkylidene groups having 1, 2, 3 or 4 carbon atoms. Methylene, ethylidene, propylidene, isopropylidene and butylidene, including sec-butylidene and iso-butylidene are particularly preferred alkylidene groups in the compounds of the present invention. Another preferred class of alkylidene groups has from 6 to about 10 carbon atoms; and even more preferably 7, 8 or 9 carbon atoms. Heptylidene, octylidene and nonylidene are the most preferred alkylidene groups of this class.

Preferred cycloalkyl groups in the compounds of the present invention have from 3 to about 12 carbon atoms. One more preferred class of cycloalkyl groups has from 3 to about 6 carbon atoms. Even more preferred are cycloalkyl groups having 3, 4 or 5 carbon atoms.

Suitable aryl groups in the compounds of the present invention include single and multiple ring compounds, including multiple ring compounds that contain separate and/or fused aryl groups. Typical aryl groups contain from 1 to 3 separated or fused rings and from 6 to about 18 carbon ring atoms. Preferably aryl groups contain from 6 to about 10 carbon ring atoms. Specially preferred aryl groups include substituted or unsubstituted phenyl, substituted or unsubstituted naphthyl, substituted or unsubstituted biphenyl, substituted or unsubstituted phenanthryl and substituted or unsubstituted anthryl.

Suitable heterocyclic groups include heteroaromatic and heteroalicyclic groups containing from 1 to 3 separated or fused rings and from 5 to about 18 ring atoms. Preferably heteroaromatic and heteroalicyclic groups contain from 5 to about 10 ring atoms. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothiophenyl, benzothiazolyl, benzoxazolyl, quinazolinyl, quinoxalinyl, naphthyridinyl and furopyridyl. Suitable heteroalicyclic groups in the compounds of the present invention contain one, two or three heteroatoms selected from N, O or S atoms and include, e.g., pyrrolidinyl, tetrahydrofuranyl, dihydrofuranyl, tetrahydrothienyl, tetrahydrothiopyranyl, piperidyl, morpholinyl, thiomorpholinyl, thioxanyl, piperazinyl, azetidinyl, oxetanyl, thietanyl, homopiperidyl, oxepanyl, thiepanyl, oxazepinyl, diazepinyl, thiazepinyl, 1,2,3,6-tetrahydropyridyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl, and quinolizinyl.

Heterocyclylalkyl groups are alkyl groups substituted with heterocyclic group wherein the alkyl and heterocyclic groups are as defined above.

The groups above mentioned may be substituted at one or more available positions by one or more suitable groups such as OR', =O, SR', SOR', SO$_2$R', NO$_2$, NHR', N(R')$_2$, =N—R', NHCOR', N(COR')$_2$, NHSO$_2$R', NR'C(=NR') NR'R', CN, halogen, COR', COOR', OCOR', OCONHR', OCON(R')$_2$, protected OH, protected amino, protected SH, substituted or unsubstituted aryl, and substituted or unsubstituted heterocyclic group, wherein each of the R' groups is independently selected from the group consisting of hydrogen, OH, NO$_2$, NH$_2$, SH, CN, halogen, COH, COalkyl, CO$_2$H, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl, and substituted or unsubstituted heterocyclic group. Where such groups are themselves substituted, the substituents may be chosen from the foregoing list.

Suitable halogen substituents in the compounds of the present invention include F, Cl, Br and I.

Suitable protecting groups are well known for the skill person in the art. A general review of protecting groups in organic chemistry is provided by Wuts, P. G. M. and Greene T. W. in Protecting groups in Organic Synthesis, 4th Ed. Wiley-Interscience, and by Kocienski P. J. in Protecting Groups, 3$^{rd}$ Ed. Georg Thieme Verlag. These references provide sections on protecting groups for OH, amino, and SH groups. All these references are incorporated by reference in their entirety. Examples of such protected OH include ethers, silyl ethers, esters, sulfonates, sulfenates and sulfinates, carbonates and carbamates. In the case of ethers the protecting group for the OH can be selected from methyl, methoxymethyl, methylthiomethyl, (phenyldimethylsilyl)methoxymethyl, benzyloxymethyl, p-methoxybenzyloxymethyl, [(3,4-dimethoxybenzyl)oxy]methyl, p-nitrobenzyloxymethyl, o-nitrobenzyloxymethyl, [(R)-1-(2-nitrophenyl)ethoxy]methyl, (4-methoxyphenoxy)methyl, guaiacolmethyl, [(p-phenylphenyl)oxy]methyl, t-butoxymethyl, 4-pentenyloxymethyl, siloxymethyl, 2-methoxyethoxymethyl, 2-cyanoethoxymethyl, bis(2-chloroethoxy)methyl, 2,2,2-trichloroethoxymethyl, 2-(trimethylsilyl)ethoxymethyl, menthoxymethyl, o-bis(2-acetoxyethoxy)methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxide, 1-[(2-chloro-4-methyl)phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydrofuranyl, tetrahydrothiofuranyl, 2,3,3α,4,5,6,7,7α-octahydro-7,8,8-trimethyl-4,7-methanobenzofuran-2-yl, 1-ethoxyethyl, 1-(2-chloroethoxy)ethyl, 2-hydroxyethyl, 2-bromoethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 1-(2-cyanoethoxy)ethyl, 2-trimethylsilylethyl, 2-(benzylthio)ethyl, 2-phenylselenyl) ethyl, t-butyl, cyclohexyl, 1-methyl-1'-cyclopropylmethyl, allyl, prenyl, cinnamyl, 2-phenallyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, p-methoxybenzyl, 3,4-dimethoxybenzyl, 2,6-dimethoxybenzyl, o-nitrobenzyl, p-nitrobenzyl, pentadienylnitrobenzyl, pentadienylnitropiperonyl, halobenzyl, 2,6-dichlorobenzyl, 2,4-dichlorobenzyl, 2,6-difluorobenzyl, p-cyanobenzyl, fluorous benzyl, 4-fluorousalkoxybenzyl, trimethylsilylxylyl, p-phenylbenzyl, 2-phenyl-2-propyl, p-acylaminobenzyl, p-azidobenzyl, 4-azido-3-chlorobenzyl, 2-trifluoromethylbenzyl, 4-trifluoromethylbenzyl, p-(methylsulfinyl)benzyl, p-siletanylbenzyl, 4-acetoxybenzyl, 4-(2-trimethylsilyl) ethoxymethoxybenzyl, 2-naphthylmethyl, 2-picolyl, 4-picolyl, 3-methyl-2-picolyl N-oxido, 2-quinolinylmethyl, 6-methoxy-2-(4-methylphenyl-4-quinolinemethyl, 1-pyrenylmethyl, diphenylmethyl, 4-methoxydiphenylmethyl, 4-phenyldiphenylmethyl, p,p'-dinitrobenzhydryl, 5-dibenzosuberyl, triphenylmethyl, tris(4-t-butylphenyl)methyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 4,4'-dimethoxy-3"-[N-(imidazolylmethyl)]trityl, 4,4'-dimethoxy-3"-[N-(imidazolylethyl)carbamoyl]trityl, bis(4-methoxyphenyl)-1'-pyrenylmethyl, 4-(17-tetrabenzo[a,c,g,i]fluorenylmethyl)-4,4"-dimethoxytrityl, 9-anthryl, 9-(9-phenyl)xanthenyl, 9-phenylthioxanthyl, 9-(9-phenyl-10-oxo)anthryl, 1,3-benzodithiolan-2-yl, and 4,5-bis(ethoxycarbonyl)-[1,3]-dioxolan-2-yl, benzisothiazolyl S,S-dioxide. In the case of silyl ethers the protecting group for the OH can be selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl. In the case of esters the protecting group for the OH can be selected from formate, benzoylformate, acetate, chloroacetate, dichloroacetate, trichloroacetate, trichloroacetamidate, trifluoroacetate, methoxyacetate, triphenylmethoxyacetate, phenoxyacetate, p-chlorophenoxyacetate, phenylacetate, diphenylacetate, 3-phenylpropionate, bisfluorous chain type propanoyl, 4-pentenoate, 4-oxopentanoate, 4,4-(ethylenedithio)pentanoate, 5[3-bis(4-methoxyphenyl)hydroxymethylphenoxy]levulinate, pivaloate, 1-adamantoate, crotonate, 4-methoxycrotonate, benzoate, p-phenylbenzoate, 2,4,6-trimethylbenzoate, 4-bromobenzoate, 2,5-difluorobenzoate, p-nitrobenzoate, picolinate, nicotinate, 2-(azidomethyl)benzoate, 4-azidobutyrate, (2-azidomethyl)phenylacetate, 2-{[(tritylthio)oxy]methyl}benzoate, 2-{[(4-methoxytritylthio)oxy]methyl}benzoate, 2-{[methyl(tritylthio)amino] methyl}benzoate, 2-{{[(4-methoxytrityl)thio]methylamino}-methyl}benzoate, 2-(allyloxy)phenylacetate, 2-(prenyloxymethyl)benzoate, 6-(levulinyloxymethyl)-3-methoxy-2-nitrobenzoate, 6-(levulinyloxymethyl)-3-methoxy-4-nitrobenzoate, 4-benzyloxybutyrate, 4-trialkylsilyloxybutyrate, 4-acetoxy-2,2-dimethylbutyrate, 2,2-dimethyl-4-pentenoate, 2-iodobenzoate, 4-nitro-4-methylpentanoate, o-(dibromomethyl)benzoate, 2-formylbenzenesulfonate, 4-(methylthiomethoxy)butyrate, 2-(methylthiomethoxymethyl)benzoate, 2-(chloroacetoxymethyl)benzoate, 2-[(2-chloroacetoxy)ethyl]benzoate, 2-[2-(benzyloxy)ethyl]benzoate, 2-[2-(4-methoxybenzyloxy)ethyl]benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, and 2-chlorobenzoate. In the case of sulfonates, sulfenates and sulfinates the protecting group for the OH can be selected from sulfate, allylsulfonate, methanesulfonate, benzylsulfonate, tosylate, 2-[(4-nitrophenyl)ethyl]sulfonate, 2-trifluoromethylbenzenesulfonate, 4-monomethoxytritylsulfenate, alkyl 2,4-dinitrophenylsulfenate, 2,2,5,5-tetramethylpyrrolidin-3-one-1-sulfinate, borate, and dimethylphosphinothioyl. In the case of carbonates the protecting group for the OH can be selected from methyl carbonate, methoxymethyl carbonate, 9-fluorenylmethyl carbonate, ethyl carbonate, bromoethyl carbonate, 2-(methylthiomethoxy)ethyl carbonate, 2,2,2-trichloroethyl carbonate, 1,1-dimethyl-2,2,2-trichloroethyl carbonate, 2-(trimethylsilyl)ethyl carbonate, 2-[dimethyl(2-naphthylmethyl)silyl]ethyl carbonate, 2-(phenylsulfonyl)ethyl carbonate, 2-(triphenylphosphonio)ethyl carbonate, cis-[4-[[(methoxytrityl)sulfenyl]oxy]tetrahydrofuran-3-yl]oxy carbonate, isobutyl carbonate, t-butyl carbonate, vinyl carbonate, allyl carbonate, cinnamyl carbonate, propargyl carbonate, p-chlorophenyl carbonate, p-nitrophenyl carbonate, 4-ethoxy-1-naphthyl carbonate, 6-bromo-7-hydroxycoumarin-4-ylmethyl carbonate, benzyl carbonate, o-nitrobenzyl carbonate, p-nitrobenzyl carbonate, p-methoxybenzyl carbonate, 3,4-dimethoxybenzyl carbonate, anthraquinon-2-ylmethyl carbonate, 2-dansylethyl carbonate, 2-(4-nitrophenyl)ethyl carbonate, 2-(2,4-dinitrophenyl)ethyl carbonate, 2-(2-nitrophenyl)propyl carbonate, alkyl 2-(3,4-methylenedioxy-6-nitrophenyl)propyl carbonate, 2-cyano-1-phenylethyl carbonate, 2-(2-pyridyl)amino-1-phenylethyl carbonate, 2-[N-methyl-N-(2-pyridyl)]amino-1-phenylethyl carbonate, phenacyl carbonate, 3',5'-dimethoxybenzoin carbonate, methyl dithiocarbonate, and S-benzyl thiocarbonate. And in the case of carbamates the protecting group for the OH can be selected from dimethylthiocarbamate, N-phenylcarbamate, N-methyl-N-(o-nitrophenyl)carbamate.

Examples of protected amino groups include carbamates, ureas, amides, heterocyclic systems, N-alkyl amines, N-alkenyl amines, N-alkynyl amines, N-aryl amines, imines, enamines, N-metal derivatives, N—N derivatives, N—P derivatives, N—Si derivatives, and N—S derivatives. In the case of carbamates the protecting group for the amino group can be selected from methylcarbamate, ethylcarbamate, 9-fluorenylmethylcarbamate, 2,6-di-t-butyl-9-fluorenylmethylcarbamate, 2,7-bis(trimethylsilyl)fluorenylmethylcarbamate, 9-(2-sulfo)fluorenylmethyl carbamate, 9-(2,7-dibromo)fluorenylmethylcarbamate, 17-tetrabenzo[a,c,g,i]fluorenylmethylcarbamate, 2-chloro-3-indenylmethylcarbamate, benz[f]inden-3-ylmethylcarbamate, 1,1-dioxobenzo[b]thiophene-2-ylmethylcarbamate, 2-methylsulfonyl-3-phenyl-1-prop-2-enyloxycarbamate, 2,7-di-t-butyl-[9,(10,10-dioxo-10,10,10, 10-tetrahydrothioxanthyl)]methylcarbamate, 2,2,2-trichloroethylcarbamate, 2-trimethylsilylethylcarbamate, (2-phenyl-2-trimethylsilyl)ethylcarbamate, 2-phenylethylcarbamate, 2-chloroethylcarbamate, 1,1-dimethyl-2-haloethylcarbamate, 1,1-dimethyl-2,2-dibromoethylcarbamate, 1,1-dimethyl-2,2,2-trichloroethylcarbamate, 2-(2'-pyridyl)ethylcarbamate, 2-(4'-pyridyl)ethylcarbamate, 2,2-bis(4'-nitrophenyl)ethylcarbamate, 2-[(2-nitrophenyl)dithio]-1-phenylethylcarbamate, 2-(N,N-dicyclohexylcarboxamido)ethylcarbamate, t-butylcarbamate, $C_8F_{19}CH_2CH_2C(CH_3)_2$-carbamate, 1-adamantylcarbamate, 2-adamantyl carbamate, 1-(1-adamantyl)-1-methylethylcarbamate, 1-methyl-1-(4-byphenylyl)ethylcarbamate, 1-(3,5-di-t-butylphenyl)-1-methylethylcarbamate, triisopropylsiloxyl carbamate, vinylcarbamate, allylcarbamate, prenylcarbamate, 1-isopropylallylcarbamate, cinnamylcarbamate, 4-nitrocinnamylcarbamate, 3-(3'-pyridyl)prop-2-enylcarbamate, hexadienyloxycarbamate, propargyloxycarbamate, but-2-ynylbisoxycarbamate, 8-quinolylcarbamate, N-hydroxypiperidinylcarbamate, alkyldithiocarbamate, benzylcarbamate, 3,5-di-t-butylbenzylcarbamate, p-methoxybenzylcarbamate, p-nitrobenzylcarbamate, p-bromobenzylcarbamate, p-chlorobenzylcarbamate, 2,4-dichlorobenzylcarbamate, 4-methylsulfinylbenzylcarbamate, 4-trifluoromethylbenzylcarbamate, $C_8F_{17}CH_2CH_2$-carbamate, $(C_8F_{17}CH_2CH_2)_3Si$-carbamate, 2-naphthylmethylcarbamate, 9-anthrylmethylcarbamate, diphenylmethylcarbamate, 4-phenylacetoxybenzylcarbamate, 4-azidobenzylcarbamate, 4-azidomethoxybenzylcarbamate, m-chloro-p-acyloxybenzylcarbamate, p-(dihydroxyboryl)benzylcarbamate, 5-benzisoxazolylmethylcarbamate, 2-(trifluoromethyl)-6-chromonylmethylcarbamate, 2-methylthioethylcarbamate, 2-methylsulfonylethylcarbamate, 2-(p-toluenesulfonyl)ethylcarbamate, 2-(4-nitrophenylsulfonyl)ethylcarbamate, 2-(2,4-dinitrophenylsulfonyl)ethoxycarbamate, 2-(4-trifluoromethylphenylsulfonyl)ethylcarbamate, [2-(1,3-dithianyl)]methylcarbamate, 2-phosphonioethylcarbamate, 2-[phenyl(methyl)sulfonio]ethylcarbamate, 1-methyl-1-(triphenylphosphonio)ethylcarbamate, 1,1-dimethyl-2-cyanoethylcarbamate, 2-dansylethylcarbamate, 2-(4-nitrophenyl)ethylcarbamate, 4-methyl-thiophenylcarbamate, 2,4-dimethylthiophenylcarbamate, m-nitrophenylcarbamate, 3,5-dimethoxybenzylcarbamate, 1-methyl-1-(3,5-dimethoxyphenyl)ethylcarbamate, α-methylnitropiperonylcarbamate, o-nitrobenzylcarbamate, 3,4-dimethoxy-6-nitrobenzylcarbamate, phenyl(o-nitrophenyl)methylcarbamate, 2-nitrophenylethylcarbamate, 6-nitroveratrylcarbamate, 4-methoxyphenacylcarbamate, 3',5'-dimethoxybenzoincarbamate, 9-xanthenylmethylcarbamate, N-methyl-N-(o-nitrophenyl)carbamate, N-(2-acetoxyethyl)aminecarbamate, t-amylcarbamate, 1-methylcyclobutylcarbamate, 1-methylcyclohexylcarbamate, 1-methyl-1-cyclopropylmethylcarbamate, cyclobutylcarbamate, cyclopentylcarbamate, cyclohexylcarbamate, isobutylcarbamate, isobornylcarbamate, cyclopropylmethylcarbamate, p-decyloxybenzylcarbamate, diisopropylmethylcarbamate, 2,2-dimethoxycarbonylvinylcarbamate, o-(N,N-dimethylcarboxamido)benzylcarbamate, 1,1-dimethyl-3-(N,N-dimethylcarboxamido)propylcarbamate, butynylcarbamate, 1,1-dimethylpropynylcarbamate, 2-iodoethylcarbamate, 1-methyl-1-(4'-pyridyl)ethylcarbamate, 1-methyl-1-(p-phenylazophenyl)ethylcarbamate, p-(p'-methoxyphenylazo)benzylcarbamate, p-(phenylazo)benzylcarbamate, 2,4,6-trimethylbenzylcarbamate, isonicotinylcarbamate, 4-(trimethyl-ammonium)benzylcarbamate, p-cyanobenzylcarbamate, di(2-pyridyl)methylcarbamate, 2-furanylmethylcarbamate, phenylcarbamate, 2,4,6-tri-t-butylphenylcarbamate, 1-methyl-1-phenylethylcarbamate, and S-benzyl thiocarbamate. In the case of ureas the protecting groups for the amino group can be selected from phenothiazinyl-(10)-carbonyl, N'-p-toluenesulfonylaminocarbonyl, N'-phenylaminothio-carbonyl, 4-hydroxyphenylaminocarbonyl, 3-hydroxytryptaminocarbonyl, and N'-phenyl-aminothiocarbonyl. In the case of amides the protecting group for the amino group can be selected from formamide, acetamide, chloroacetamide, trichloroacetamide, trifluoroacetamide, phenylacetamide, 3-phenylpropanamide, pent-4-enamide, picolinamide, 3-pyridylcarboxamide, N-benzoylphenylalanyl, benzamide, p-phenylbenzamide, o-nitrophenylacetamide, 2,2-dimethyl-2-(o-nitrophenyl)acetamide, o-nitrophenoxyacetamide, 3-(o-nitrophenyl)propanamide, 2-methyl-2-(o-nitrophenoxy)propanamide, 3-methyl-3-nitrobutanamide, o-nitrocinnamide, o-nitrobenzamide, 3-(4-t-butyl-2,6-dinitrophenyl)-2,2-dimethylpropanamide, o-benzoyloxymethyl)benzamide, 2-(acetoxymethyl)benzamide, 2-[(t-butyldiphenylsiloxy)methyl]benzamide, 3-(3',6'-dioxo-2',4',5'-trimethylcyclohexa-1',4'-diene)-3,3-dimethylpropanamide, o-hydroxy-trans-cinnamide, 2-methyl-2-(o-phenylazophenoxy)propanamide, 4-chlorobutanamide, acetoacetamide, 3-(p-hydroxyphenyl)propanamide, (N-dithiobenzyloxycarbonylamino)acetamide, and N-acetylmethioninamide. In the case of heterocyclic systems the protecting group for the amino group can be selected from 4,5-diphenyl-3-oxazolin-2-one, N-phthalimide, N-dichlorophthalimide, N-tetrachlorophthalimide, N-4-nitrophthalimide, N-thiodiglycoloyl, N-dithiasuccinimide, N-2,3-diphenylmaleimide, N-2,3-dimethylmaleimide, N-2,5-dimethylpyrrole, N-2,5-bis(thisopropylsiloxy)pyrrole, N-1,1,4,4-tetramethyldisilylazacyclopentane adduct, N-1,1,3,3-tetramethyl-1,3-disilaisoindoline, N-diphenylsilyldiethylene, N-5-substituted-1,3-dimethyl-1,3,5-triazacyclohexan-2-one, N-5-substituted-1,3-benzyl-1,3,5-triazacyclohexan-2-one, 1-substituted 3,5-dinitro-4-pyridone, and 1,3,5-dioxazine. In the case of N-alkyl, N-alkenyl, N-alkynyl or N-aryl amines the protecting group for the amino group can be selected from N-methyl, N-t-butyl, N-allyl, N-prenyl, N-cinnamyl, N-phenylallyl, N-propargyl, N-methoxymethyl, N-[2-(trimethylsilyl)ethoxy]methyl, N-3-acetoxypropyl, N-cyanomethyl, 2-azanorbornenes, N-benzyl, N-4-methoxybenzyl, N-2,4-dimethoxybenzyl, N-2-hydroxybenzyl, N-ferrocenylmethyl, N-2,4-dinitrophenyl, o-methoxyphenyl, p-methoxyphenyl, N-9-phenylfluorenyl, N-fluorenyl, N-2-picolylamine N'-Oxide, N-7-methoxycoumar-4-ylmethyl, N-diphenylmethyl, N-bis(4-methoxyphenyl)methyl, N-5-dibenzosuberyl, N-triphenylmethyl, N-(4-methylphenyl)diphenylmethyl, and N-(4-methoxyphenyl)diphenylmethyl. In the case of imines the protecting group for the amino group can be selected from N-1,1-dimethylthiomethylene, N-benzylidene, N-p-methoxybenzylidene, N-diphenylmethylene, N-[2-pyridyl)mesityl]methylene, N—(N',N'-dimethylaminomethylene), N—(N',N'-dibenzylaminomethylene), N—(N'-t-butylaminomethylene), N,N'-isopropylidene, N-p-nitrobenzylidene, N-salicylidene, N-5-chlorosalicylidene, N-(5-chloro-2-hydroxyphenyl)phenylmethylene, N-cyclohexylidene, and N-t-butylidene. In the case of enamines the protecting group for the amino group can be selected from N-(5,5-dimethyl-3-oxo-1-cyclohexenyl), N-2,7-dichloro-9-fluorenylmethylene, N-1-(4,4-dimethyl-2,6-dioxocyclohexylidene)ethyl, N-(1,3-dimethyl-2,4,6-(1H, 3H, 5H)-trioxopyrimidine-5-ylidenyl) methyl, N-4,4,4-trifluoro-3-oxo-1-butenyl, and N-(1-isopropyl-4-nitro-2-oxo-3-pyrrolin-3-yl). In the case of N-metal derivatives the protecting group for the amino group can be selected from N-diphenylborinic acid, N-diethylborinic acid, N-9-borabicyclononane, N-difluoroborinic acid, and 3,5-bis (trifluoromethyl)phenylboronic acid; and also including N-[phenyl(pentacarbonylchromium)]carbenyl, N-[phenyl (pentacarbonyltungsten)]carbenyl, N-[methyl(pentacarbonylchromium)]carbenyl, N-[methyl(pentacarbonyltungsten)]-carbenyl, N-copper chelate, N-zinc chelate, and a 18-crown-6-derivative. In the case of N—N derivatives the protecting group for the amino group can be selected from N-nitro, N-nitroso, N-oxide, azide, triazene, and N-trimethylsilylmethyl-N-benzylhydrazine. In the case of N—P derivatives the protecting group for the amino group can be selected from N-diphenylphosphinamide, dimethylthiophosphinamide, diphenylthiophosphinamide, dialkyl phosphoramidate, dibenzyl phosphoramidate, diphenyl phosphoramidate, and iminotriphenylphosphorane. In the case of N—Si derivatives the protecting group for the $NH_2$ can be selected from t-butyldiphenylsilyl and triphenylsilyl. In the case of N—S derivatives the protecting group for the amino group can be selected from N-sulfenyl or N-sulfonyl derivatives. The N-sulfenyl derivatives can be selected from benzenesulfenamide, 2-nitrobenzenesulfenamide, 2,4-dinitrobenzenesulfenamide, pentachlorobenzenesulfenamide, 2-nitro-4-methoxybenzenesulfanamide, triphenylmethylsulfenamide, 1-(2,2,2)-trifluoro-1,1-diphenyl)ethylsulfenamide, and N-3-nitro-2-pyridinesulfenamide. The N-sulfonyl derivatives can be selected from methanesulfonamide, trifluoromethanesulfonamide, t-butylsulfonamide, benzylsulfonamide, 2-(trimethylsilyl)ethanesulfonamide, p-toluenesulfonamide, benzenesulfonamide, anisylsulfonamide, 2-nitrobenzenesulfonamide, 4-nitrobenzenesulfonamide, 2,4-dinitrobenzenesulfonamide, 2-naphthalenesulfonamide, 4-(4',8'-dimethoxynaphthylmethyl)benzenesulfonamide, 2-(4-methylphenyl)-6-methoxy-4-methylsulfonamide, 9-anthracenesulfonamide, pyridine-2-sulfonamide, benzothiazole-2-sulfonamide, phenacylsulfonamide, 2,3,6-trimethyl-4-methoxybenzenesulfonamide, 2,4,6-trimethoxybenzenesulfonamide, 2,6-dimethyl-4-methoxybenzenesulfonamide, pentamethylbenzenesulfonamide, 2,3,5,6-tetramethyl-4-methoxybenzenesulfonamide, 4-methoxybenzenesulfonamide, 2,4,6-trimethylbenzenesulfonamide, 2,6-dimethoxy-4-methylbenzenesulfonamide, 3-methoxy-4-t-butylbenzenesulfonamide, and 2,2,5,7,8-pentamethylchroman-6-sulfonamide. Examples of such protected SH include thioethers, disulfides, silyl thioethers, thioesters, thiocarbonates, and thiocarbamates. In the case of thioethers the protecting group for the SH can be selected from S-alkyl, S-benzyl, S-acetamidomethyl (Acm), S-p-methoxybenzyl, S-o-hydroxybenzyl, S-p-hydroxybenzyl, S-o-methoxybenzyl, S-p-methoxybenzyl, S-p-nitrobenzyl, S-o-nitrobenzyl, S-2,4,6-trimethoxybenzyl, S-4-picolyl, S-2-picolyl-N-oxide, S-2-quinolinylmethyl, S-9-anthrylmethyl, S-9-fluorenylmethyl, S-xanthenyl, S-ferrocenylmethyl, S-diphenylmethyl, S-bis(4-methoxyphenyl)methyl, S-5-dibenzosuberyl, S-triphenylmethyl, 4-methoxytrityl, S-diphenyl-4-pyridylmethyl, S-2,4-dinitrophenyl, S-2-quinolyl, S-t-butyl, S-1-adamantyl, S-methoxymethyl monothioacetal, S-isobutoxymethyl monothioacetal, S-benzyloxymethyl, S-1-ethoxyethyl, S-tetrahydropyranyl monothioacetal, S-benzylthiomethyl dithioacetal, Thiazolidine derivative, S-acetamidomethyl aminothioacetal, S-trimethylacetamidomethyl aminothioacetal, S-benzamidomethyl aminothioacetal, 5-allyloxycarbonylaminomethyl, S—N-[2, 3,5,6-tetrafluoro-4-(N-piperidino)-phenyl-N-allyloxycarbonylaminomethyl, S-phthalimidomethyl, 5-phenylacetamidomethyl, 5-(2-nitro-1-phenyl)ethyl, S-2-(2,4- dinitrophenyl)ethyl, S-2-(4'-pyridyl)ethyl, S-2-cyanoethyl, S-2-(trimethylsilyl)ethyl, S-2,2-b is (carboethoxy)ethyl, S-(1-m-nitrophenyl-2-benzoyl)ethyl, S-2-phenylsulfonyl-ethyl, S-1-(4-methylphenylsulfonyl)-2-methylprop-2-yl, and S-p-hydroxyphenacyl. In the case of disulfides the protecting group for the SH can be selected from S—S-tBu [S-(tert-butylsulfanyl)cysteine, S—S-tbutyl) and S-Npys (S-3-nitro-2-pyridinesulfenyl). In the case of silyl thioethers the protecting group for the SH can be selected from the list of groups that was listed above for the protection of OH with silyl ethers. In the case of thioesters the protecting group for the SH can be selected from S-acetyl, S-benzoyl, S-2-methoxyisobu-tyryl, 5-trifluoroacetyl, S—N-[[p-biphenylyl)isopropoxy]carbonyl]-N-methyl-γ-aminothiobutyrate, and S—N-(t-bu-toxycarbonyl)-N-methyl-γ-aminothiobutyrate. In the case of thiocarbonate protecting group for the SH can be selected from S-2,2,2-trichloroethoxycarbonyl, 5-t-butoxycarbonyl, S-benzyloxycarbonyl, S-p-methoxybenzyloxycarbonyl, and S-fluorenylmethylcarbonyl. In the case of thiocarbamate the protecting group for the SH can be selected from S—(N-ethylcarbamate) and S—(N-Methoxymethylcarbamate). The mention of these groups should not be interpreted as a limitation of the scope of the invention, since they have been mentioned as a mere illustration of protecting groups for OH, amino and SH groups, but further groups having said function may be known by the skill person in the art, and they are to be understood to be also encompassed by the present invention.

The terms "pharmaceutically acceptable salt", "derivative", and "prodrug" refer to any pharmaceutically acceptable salt, ester, solvate, hydrate or any other compound which, upon administration to the patient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoac-ids salts.

The compounds of the invention may be in crystalline form either as free compounds or as solvates (e.g. hydrates) and it is intended that both forms are within the scope of the present invention. Methods of solvation are generally known within the art.

Any compound that is a prodrug of a compound of formula I is within the scope and spirit of the invention. The term "prodrug" is used in its broadest sense and encompasses those derivatives that are converted in vivo to the compounds of the invention. Such derivatives would readily occur to those skilled in the art, and include, for example, compounds where a free hydroxy group is converted into an ester derivative.

Any compound referred to herein is intended to represent such specific compound as well as certain variations or forms. In particular, compounds referred to herein may have asymmetric centres and therefore exist in different enantiomeric forms. All optical isomers and stereoisomers of the compounds referred to herein, and mixtures thereof, are considered within the scope of the present invention. Thus any given compound referred to herein is intended to represent any one of a racemate, one or more enantiomeric forms, one or more diastereomeric forms, one or more atropisomeric forms, and mixtures thereof. Particularly, the compounds of the present invention represented by the above described formula I may include enantiomers depending on their asymmetry or diastereoisomers. Stereoisomerism about the double bond is also possible, therefore in some cases the molecule could exist as (E)-isomer or (Z)-isomer. If the molecule contains several double bonds, each double bond will have its own stereoisomerism, that could be the same or different than the stereoisomerism of the other double bonds of the molecule. The single isomers and mixtures of isomers fall within the scope of the present invention.

Furthermore, compounds referred to herein may exist as geometric isomers (i.e., cis and trans isomers), as tautomers, or as atropoisomers. Specifically, the term tautomer refers to one of two or more structural isomers of a compound that exist in equilibrium and are readily converted from one isomeric form to another. Common tautomeric pairs are amine-imine, amide-imide, keto-enol, lactam-lactim, etc. Additionally, any compound referred to herein is intended to represent hydrates, solvates, and polymorphs, and mixtures thereof when such forms exist in the medium. In addition, compounds referred to herein may exist in isotopically-labelled forms. All geometric isomers, tautomers, atropisomers, hydrates, solvates, polymorphs, and isotopically labelled forms of the compounds referred to herein, and mixtures thereof, are considered within the scope of the present invention.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

In compounds of general formula I, particularly preferred $R_1$ and $R_6$ are each independently hydrogen or substituted or unsubstituted $C_1$-$C_{12}$ alkyl; and more preferred are each independently hydrogen or substituted or unsubstituted alkyl group selected from methyl, ethyl, propyl, isopropyl and butyl, including isobutyl, sec-butyl and tert-butyl. Particularly preferred $R_1$ and $R_6$ are each independently methyl, methylthiomethyl, or isopropyl, being methylthiomethyl the most preferred $R_1$ and $R_6$.

Particularly preferred $R_4$ and $R_9$ are each independently hydrogen or substituted or unsubstituted $C_1$-$C_{12}$ alkyl; and more preferred are each independently hydrogen or substituted or unsubstituted alkyl group selected from methyl, ethyl, propyl, isopropyl and butyl, including isobutyl, sec-butyl and tert-butyl, being hydrogen the most preferred $R_4$ and $R_9$.

Particularly preferred $R_3$ and $R_8$ are each independently a mercaptoalkyl group wherein the mercapto group is protected, or $R_3$ and $R_8$ form a group —$CH_2$—S—S—$CH_2$—. Preferably $R_3$ and $R_8$ form a group —$CH_2$—S—S—$CH_2$—.

Particularly preferred $R_2$ and $R_7$ are hydrogen.

Particularly preferred $R_5$ and $R_{10}$ are each independently an amino protecting group or —(C=O)R" wherein each R" is independently a substituted or unsubstituted heteroaromatic group. More preferred $R_5$ and $R_{10}$ are each independently —(C=O)R" wherein each R" is independently a heteroaromatic group selected from substituted or unsubstituted cinnolinyl, substituted or unsubstituted quinolyl, substituted or unsubstituted isoquinolyl, substituted or unsubstituted naphthyridinyl, substituted or unsubstituted quinoxalinyl, and substituted or unsubstituted quinazolinyl; and even more preferred are each independently substituted or unsubstituted quinolyl and substituted or unsubstituted quinoxalinyl. Substituted or unsubstituted quinolyl is the most preferred R". Preferred substituents of said groups are OR', =O, SR', SOR', $SO_2R'$, $NO_2$, NHR', N(R')$_2$, =N—R', NHCOR', N(COR')$_2$, $NHSO_2R'$, NR'C(=NR')NR'R', CN, halogen, COR', COOR', OCOR', OCONHR', OCON(R')$_2$, protected OH, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Even more preferred substituents of the above mentioned groups are OH, $SCH_3$, SH, $NH_2$, NHC(=NH)$NH_2$, $CONH_2$, COOH, phenyl, p-, m- or o-hydroxyphenyl, indolyl, including 1-, 2-, and 3-indolyl, and imidazolyl, including 4- and 5-imidazolyl.

Particularly preferred $R_a$, $R_b$, and $R_c$ are each independently hydrogen or substituted or unsubstituted $C_1$-$C_{12}$ alkyl. More preferred $R_a$, $R_b$, and $R_c$ are each independently hydrogen or substituted or unsubstituted $C_1$-$C_6$ alkyl; and even more preferred are each independently hydrogen or methyl. Specifically, most preferred $R_a$ is methyl, $R_b$ is methyl and $R_c$ is hydrogen.

Particularly preferred $R_d$, $R_e$, and $R_f$ are each independently hydrogen or substituted or unsubstituted $C_1$-$C_{12}$ alkyl. More preferred $R_d$, $R_e$, and $R_f$ are each independently hydrogen or substituted or unsubstituted $C_1$-$C_6$ alkyl; and even more preferred are each independently hydrogen or methyl. Specifically, most preferred $R_d$ is methyl, $R_e$ is methyl and $R_f$ is hydrogen.

Particularly preferred $R_h$ is a substituted or unsubstituted $C_1$-$C_{12}$ alkyl group or a —($CH_2$—$CH_2$O)$_n$—$CH_3$ group wherein n is from 1 to 25. More preferred $R_h$ is a substituted or unsubstituted $C_1$-$C_6$ alkyl or a —($CH_2$—$CH_2$O)$_n$—$CH_3$ group wherein n is from 1 to 15. Even more preferred $R_h$ is a methyl, ethyl, propyl, or isopropyl group. Most preferred $R_h$ is methyl.

Particularly preferred Y is S or $NR_i$, and most preferred Y is $NR_i$.

Particularly preferred $R_i$ is hydrogen or substituted or unsubstituted $C_1$-$C_{12}$ alkyl or a —($CH_2$—$CH_2$O)$_n$—$CH_3$ group wherein n is from 1 to 25. More preferred $R_i$ is substituted or unsubstituted $C_1$-$C_6$ alkyl or a —($CH_2$—$CH_2$O)$_n$—$CH_3$ group wherein n is from 1 to 15. Even more preferred $R_i$ is methyl, ethyl, propyl, or isopropyl. Most preferred $R_i$ is methyl.

In another embodiment of the invention, it is also preferred that the pair $R_1$-$R_2$ and/or $R_6$-$R_7$ independently form a substituted or unsubstituted $C_1$-$C_{12}$ alkylidene or together with the corresponding C atom to which they are attached form a substituted or unsubstituted $C_3$-$C_{12}$ cycloalkyl. More preferred the pair $R_1$-$R_2$ and/or $R_6$-$R_7$ independently form a $C_1$-$C_6$ alkylidene or together with the corresponding C atom to which they are attached form a $C_3$-$C_6$ cycloalkyl. Even more preferred the pair $R_1$-$R_2$ and/or $R_6$-$R_7$ independently form a $C_1$-$C_4$ alkylidene or together with the corresponding C atom to which they are attached form a $C_3$-$C_5$ cycloalkyl. Most preferred the pair $R_1$-$R_2$ and/or $R_6$-$R_7$ independently form a methylene or together with the corresponding C atom to which they are attached form a $C_3$-cycloalkyl.

Preferred compounds of the invention are those of general formula II or pharmaceutically acceptable salts, derivatives, tautomers, prodrugs or stereoisomers thereof,

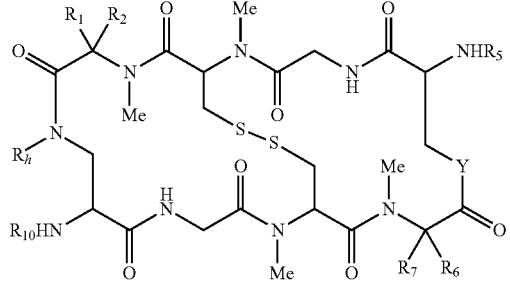

Formula II wherein $R_1$, $R_2$, $R_5$, $R_6$, $R_7$, $R_{10}$, Y, and $R_h$ groups have the same meaning given above.

In compounds of general formula II, particularly preferred $R_1$ and $R_6$ are each independently hydrogen or substituted or unsubstituted $C_1$-$C_{12}$ alkyl; and more preferred are each independently hydrogen or substituted or unsubstituted alkyl group selected from methyl, ethyl, propyl, isopropyl and butyl, including isobutyl, sec-butyl and tert-butyl. Particularly preferred $R_1$ and $R_6$ are each independently methyl, methylthiomethyl, or isopropyl, being methylthiomethyl the most preferred $R_1$ and $R_6$.

Particularly preferred $R_2$ and $R_7$ are hydrogen.

Particularly preferred $R_5$ and $R_{10}$ are each independently an amino protecting group or —(C=O)R" wherein each R" is independently a substituted or unsubstituted heteroaromatic group. More preferred $R_5$ and $R_{10}$ are each independently —(C=O)R" wherein each R" is independently a heteroaromatic group selected from substituted or unsubstituted cinnolinyl, substituted or unsubstituted quinolyl, substituted or unsubstituted isoquinolyl, substituted or unsubstituted naphthyridinyl, substituted or unsubstituted quinoxalinyl, and substituted or unsubstituted quinazolinyl; and even more preferred are each independently substituted or unsubstituted quinolyl and substituted or unsubstituted quinoxalinyl. Substituted or unsubstituted quinolyl is the most preferred R". Preferred substituents of said groups are OR', =O, SR', SOR', $SO_2R'$, $NO_2$, NHR', N(R')$_2$, =N—R', NHCOR', N(COR')$_2$, $NHSO_2R'$, NR'C(=NR')NR'R', CN, halogen, COR', COOR', OCOR', OCONHR', OCON(R')$_2$, protected OH, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Even more preferred substituents of the above mentioned groups are OH, $SCH_3$, SH, $NH_2$, NHC(=NH)$NH_2$, $CONH_2$, COOH, phenyl, p-, m- or o-hydroxyphenyl, indolyl, including 1-, 2-, and 3-indolyl, and imidazolyl, including 4- and 5-imidazolyl.

Particularly preferred $R_h$ is a substituted or unsubstituted $C_1$-$C_{12}$ alkyl group or a —($CH_2$—$CH_2$O)$_n$—$CH_3$ group wherein n is from 1 to 25. More preferred $R_h$ is a substituted or unsubstituted $C_1$-$C_6$ alkyl or a —($CH_2$—$CH_2$O)$_n$$CH_3$ group wherein n is from 1 to 15. Even more preferred $R_h$ is a methyl, ethyl, propyl or isopropyl group. Most preferred $R_h$ is methyl.

Particularly preferred Y is S or NR$_i$, and most preferred Y is NR$_i$.

Particularly preferred R$_i$ is hydrogen or substituted or unsubstituted C$_1$-C$_{12}$ alkyl or a —(CH$_2$—CH$_2$O)$_n$—CH$_3$ group wherein n is from 1 to 25. More preferred R$_i$ is substituted or unsubstituted C$_1$-C$_6$ alkyl or a —(CH$_2$—CH$_2$O)$_n$—CH$_3$ group wherein n is from 1 to 15. Even more preferred R$_i$ is methyl, ethyl, propyl, or isopropyl. Most preferred R$_i$ is methyl.

In another embodiment of the invention, it is also preferred that the pair R$_1$-R$_2$ and/or R$_6$-R$_7$ independently form a substituted or unsubstituted C$_1$-C$_{12}$ alkylidene or together with the corresponding C atom to which they are attached form a substituted or unsubstituted C$_3$-C$_{12}$ cycloalkyl. More preferred the pair R$_1$-R$_2$ and/or R$_6$-R$_7$ independently form a C$_1$-C$_6$ alkylidene or together with the corresponding C atom to which they are attached form a C$_3$-C$_6$ cycloalkyl. Even more preferred the pair R$_1$-R$_2$ and/or R$_6$-R$_7$ independently form a C$_1$-C$_4$ alkylidene or together with the corresponding C atom to which they are attached form a C$_3$-C$_5$ cycloalkyl. Most preferred the pair R$_1$-R$_2$ and/or R$_6$-R$_7$ independently form a methylene or together with the corresponding C atom to which they are attached form a C$_3$-cycloalkyl.

A particularly preferred compound of the invention is the following:

The compounds of the invention can be obtained by synthesis following known procedures for the synthesis of related compounds (Albericio et al. Int. J. of Peptide Research and Therapeutics, 2007, 13, 295-306; Albericio et al. Chem. Eur. J. 2006, 12, 9001-9009; Albericio et al. J. Am. Chem. Soc. 2007, 129, 5322-5323; Boger and Lewis, WO 02/49577; Boger and Lee, J. Org. Chem. 2000, 65, 5996-6000; Boger et al. J. Am. Chem. Soc. 2001, 123, 561-568; Lorentz and Diederichsen, J. Org. Chem. 2000, 65, 5996-6000; Dietrich and Diederichsen, Eur. J. Org. Chem. 2005, 147-153; Hae kim et al. Bioorganic Med. Chem. Lett. 2004, 14, 541-544; Malkinson et al. J. Org. Chem. 2005, 70, 7654-7661; Olsen et al. Tetrahedron, 1982, 38, 57-61; Olsen and Dhaon, J. Org. Chem. 1981, 46, 3436-3440; Olsen and Chakravarty, Pept. Struct. Biol. Funct. Proc. Am. Pept. Symp., 6th, 1979, 559-562; Olsen, J. Am. Chem. Soc. 1978, 100, 7684-7690; Chakravarty and Olsen, Tetrahedron Lett. 1978, 19, 1613-1616; Olsen and Ciardelli, J. Am. Chem. Soc. 1977, 99, 2806-1807; Olsen et al. J. Org. Chem. 1975, 40, 3110-3112; Shin et al. Bull. Chem. Soc. Japan, 1984, 57, 2203-2210; Shin et al. Bull. Chem. Soc. Japan, 1984, 57, 2211-2215; Shin et al. Bull. Chem. Soc. Japan, 1978, 51, 1501-1506; Bayó-Puxan, N. Ph. D. Thesis, University of Barcelona, 2006).

For example, two different strategies can be employed for the synthesis of compound 2.

Both strategies start with the preparation of a tetrapeptide linked to a resin, which is obtained as indicated in the Scheme 1.

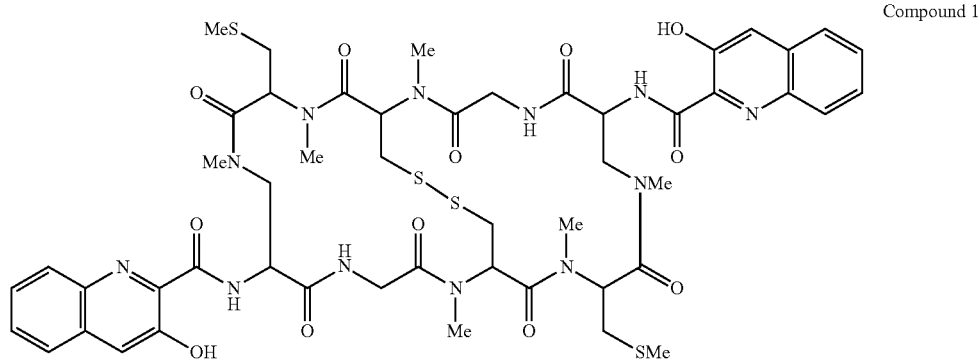 [SMILES: CSCC1C(=O)N(C)CC(NC(=O)c2nc3ccccc3cc2O)C(=O)NCC(=O)N(C)C2CSSCC(C(=O)N1C)N(C)C(=O)CNC(=O)C(NC(=O)c1nc3ccccc3cc1O)CN(C)C(=O)C(CSC)N(C)C2=O]

Compound 1

And the preferred stereoisomer of said compound is the following:

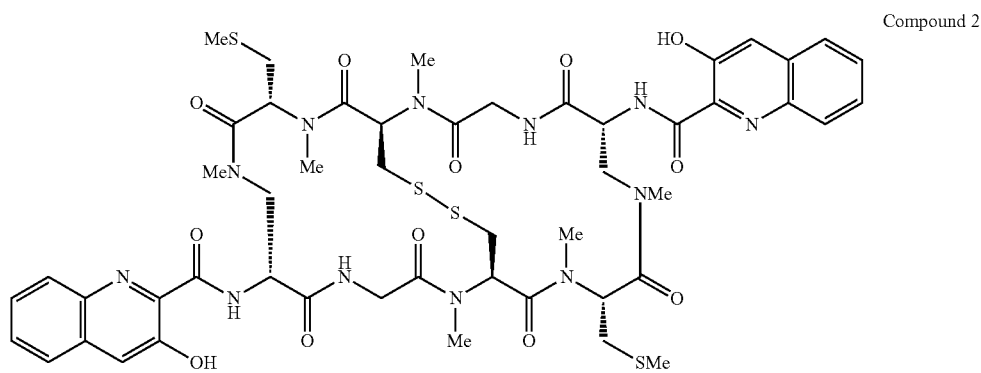 [SMILES: CSC[C@H]1C(=O)N(C)C[C@@H](NC(=O)c2nc3ccccc3cc2O)C(=O)NCC(=O)N(C)[C@H]2CSSC[C@@H](C(=O)N1C)N(C)C(=O)CNC(=O)[C@H](NC(=O)c1nc3ccccc3cc1O)CN(C)C(=O)[C@H](CSC)N(C)C2=O]

Compound 2

Scheme 1

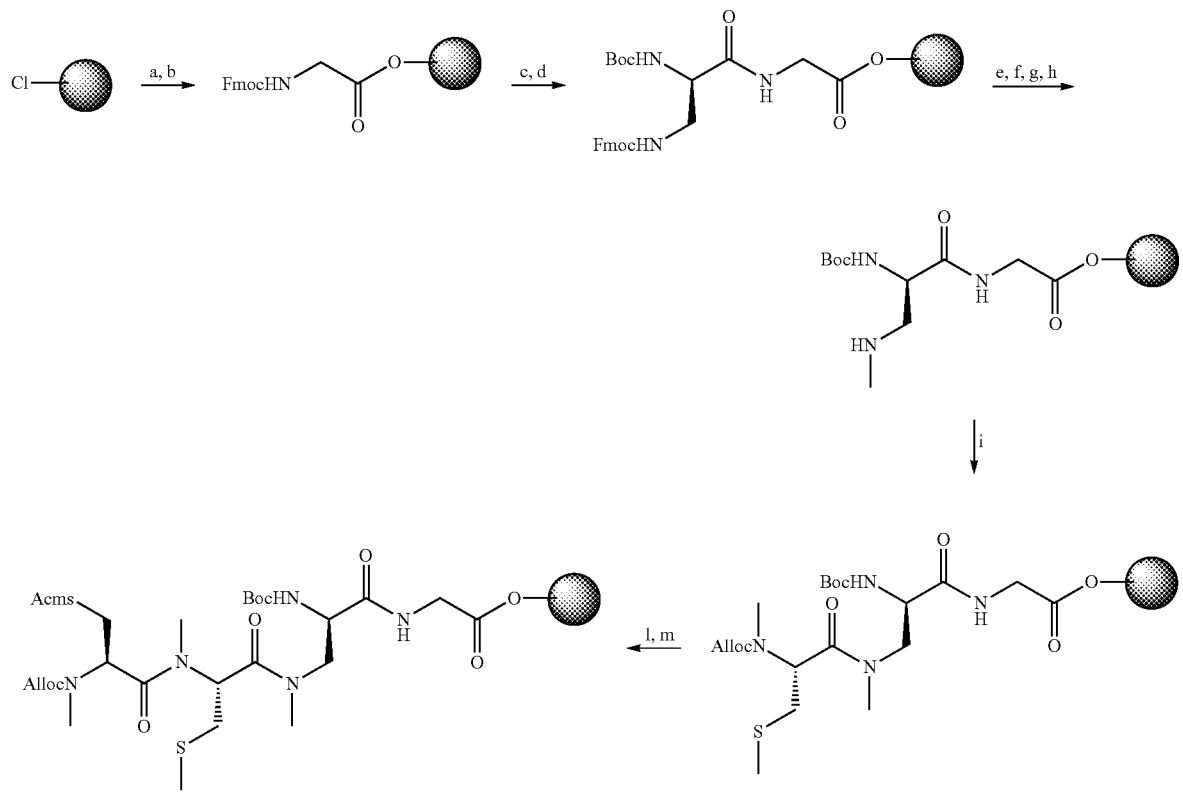

(a) Fmoc-Gly-OH, DIEA, CH$_2$Cl$_2$; (b) MeOH; (c) piperidine/DMF (1:4); (d) Boc-D-Dap(Fmoc)-OH, HATU, HOAt, DIEA, DMF; (e) piperidine/DMF (1:4), piperidine/DBU/toluene/DMF (1:1:4:14); (f) 2-NBSCl, DIEA, CH$_2$Cl$_2$; (g) PPh$_3$, DIAD, MeOH, THF; (h) HO—CH$_2$CH$_2$—SH, DBU; (i) Alloc-NMeCys(Me)-OH, HATU, HOAt, DIEA, DMF; (l) Pd(PPh$_3$)$_4$, PhSiH$_3$, CH$_2$Cl$_2$; (m) Alloc-NMeCys(Acm)-OH, HATU, HOAt, DIEA, DMF.

Strategy I

In this strategy, there is a selective deprotection of the tetrapeptide resin at its terminal amino group and, independently, cleavage of the tetrapeptide from the resin followed by the coupling of both fragments to provide, after deprotection, a linear octapeptide according to Scheme 2.

Scheme 2

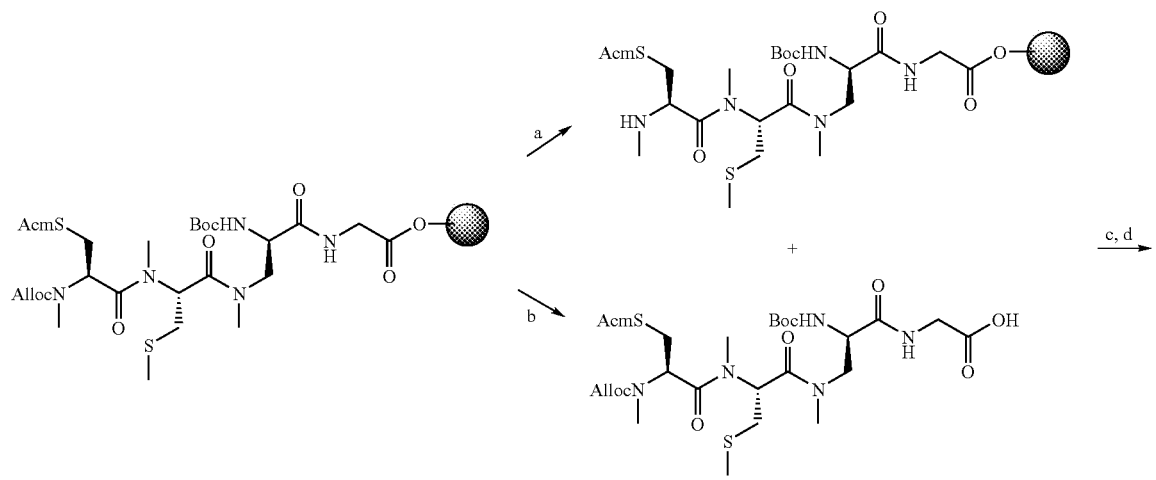

-continued

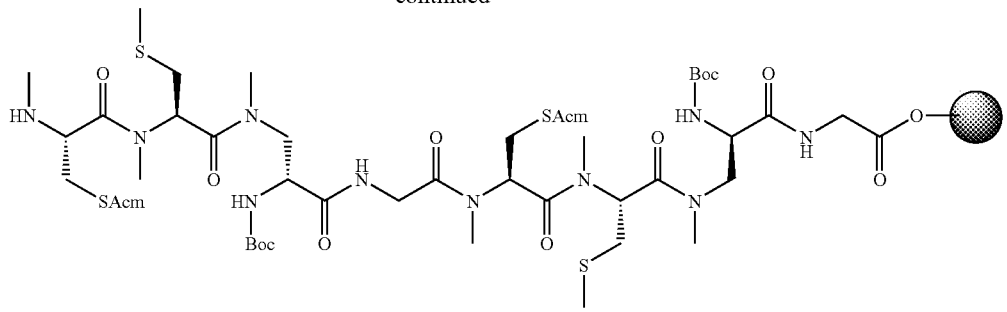

(a) Pd(PPh₃)₄, PhSiH₃, CH₂Cl₂; (b) TFA/CH₂Cl₂ (2:98); (c) PyAOP, DIEA, DMF; (d) Pd(Ph₃)₄, PhSiH₃, CH₂Cl₂.

Solid phase cyclization of the linear octapeptide through the formation of a —S—S— bridge followed by cleavage according to Scheme 3 provides a monocyclic octapeptide.

Scheme 3

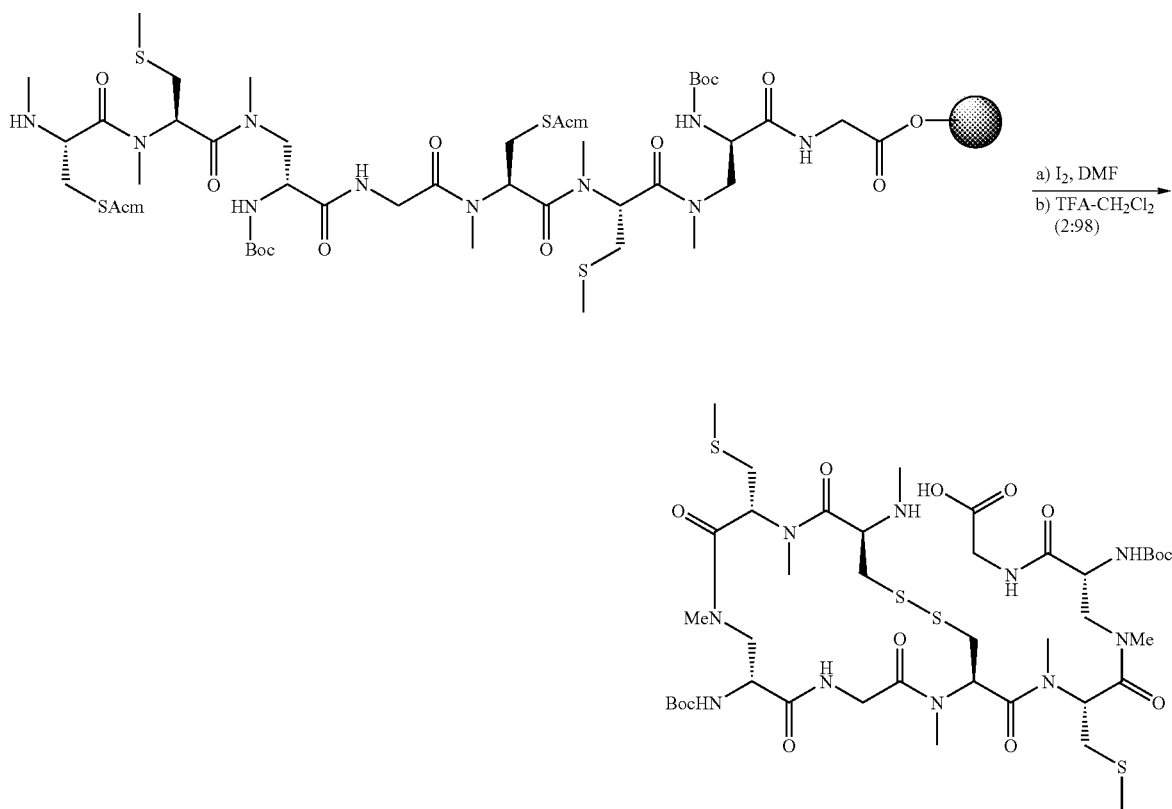

Solution cyclization of monocyclic octapeptide, followed by deprotection and coupling with 3-hydroxyquinoline-2-carboxylic acid according to Scheme 4 provides compound 2.

Scheme 4

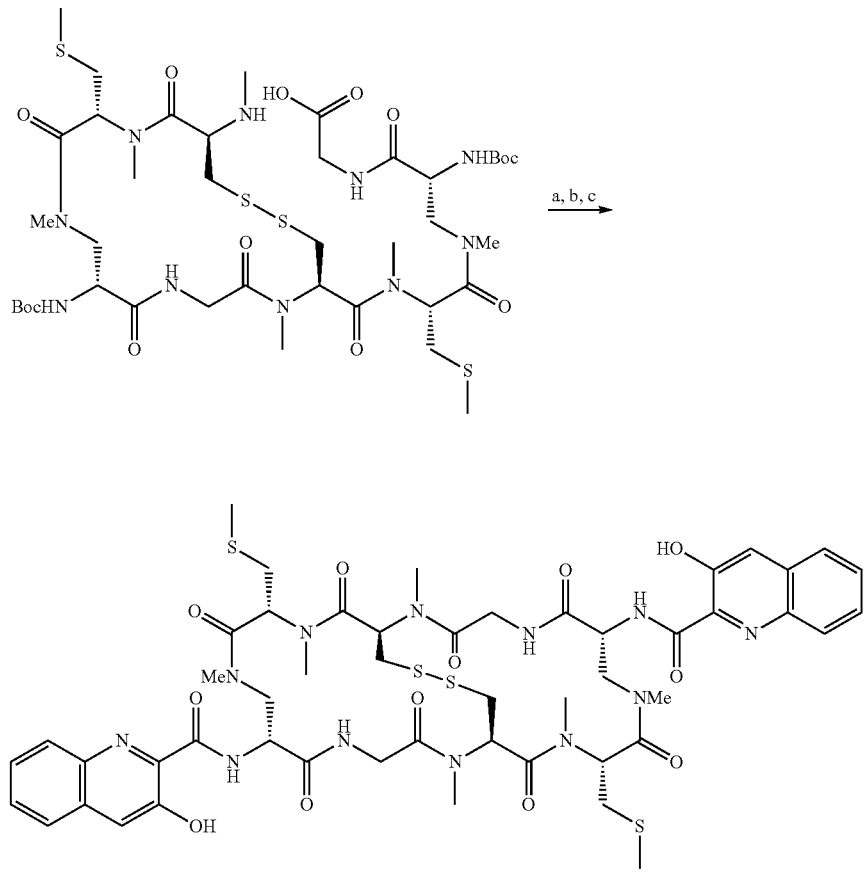

(a) EDC·HCl, HOAt, DIEA, CH₂Cl₂, DMF; (b) TFA/CH₂Cl₂ 1:1; (c) EDCl, HOSu, 3-hydroxyquinoline-2-carboxylic acid, DIEA, CH₂Cl₂

Strategy II

In this strategy, after removal of the terminal protecting group, there is a one-pot cyclization of two tetrapeptide chains in the tetrapeptide resin through the formation of a —S—S— bridge and it is followed by cleavage from the resin to provide a linear tetrapeptide dimer according to Scheme 5.

Scheme 5

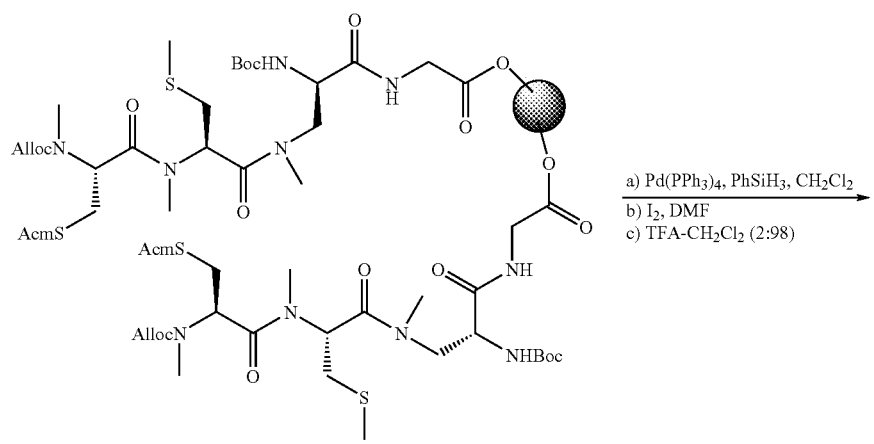

-continued

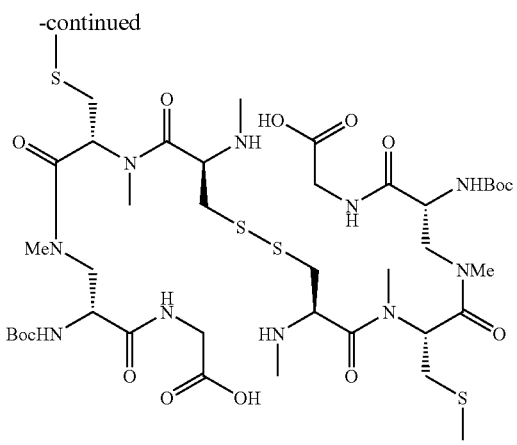

Bis-cyclization of this linear dimer via the formation of two amide bonds, followed by deprotection and coupling with 3-amino-2-quinoline carboxylic acid provides compound 2 according to Scheme 6.

to a desired substituent. Saturation or unsaturation in the ring-structure can be introduced or removed as part of the synthesis. Starting materials and reagents can be modified as desired to ensure synthesis of the intended compound. In Scheme 6

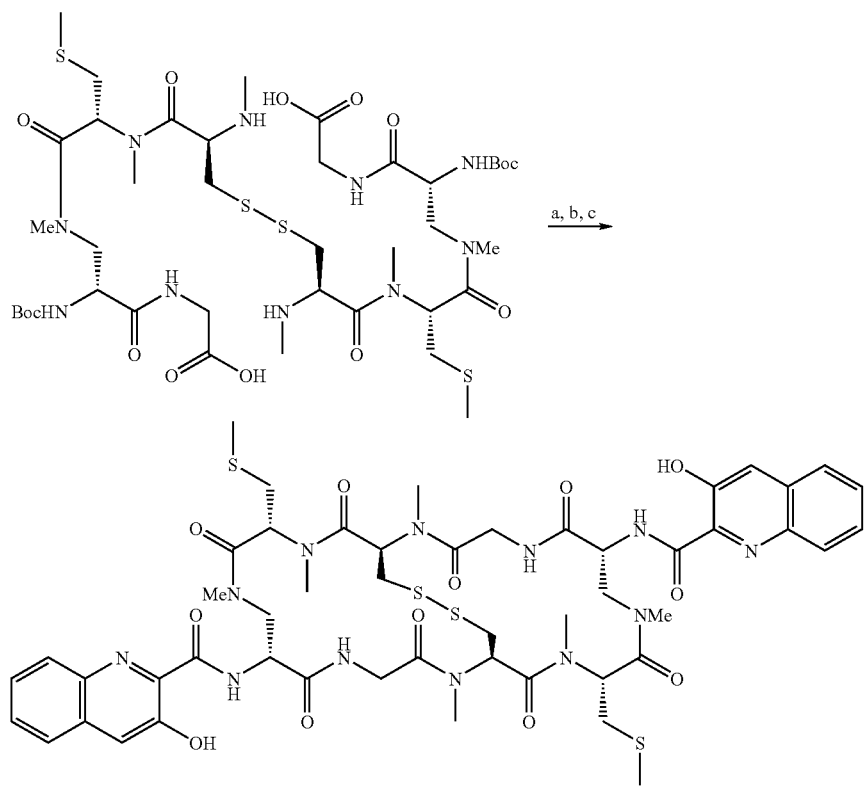

(a) PyBOP, HOAt, DIEA, CH$_2$Cl$_2$, DMF; (b) TFA/CH$_2$Cl$_2$ 1:1;
(c) EDC·HCl, HOSu, 3-hydroxyquinoline-2-carboxylic acid, DIEA, CH$_2$Cl$_2$ Analogues of compounds 1 and 2 can be synthesized by an equivalent process as those described for compound 2, by choosing the appropriate substituents of the intermediate compounds in each case.

When necessary, appropriate protecting groups can be used on the substituents to ensure that reactive groups are not affected. The synthesis can be designed to employ precursor substituents which can be converted at the appropriate stage to a desired substituent. Saturation or unsaturation in the ring-structure can be introduced or removed as part of the synthesis. Starting materials and reagents can be modified as desired to ensure synthesis of the intended compound. In addition, analogues can also be synthesized from compounds 1 and 2 by usual procedures in synthetic organic chemistry which are known by a person skilled in the art.

The synthetic routes above mentioned can be modified as desired to give stereospecific compounds as well as mixtures of stereoisomers. It is possible to synthesize specific stereoisomers or specific mixtures by various methods including the use of stereospecific reagents or by introducing chiral centers into the compounds during the synthesis. It is possible to introduce one or more stereocenters during synthesis and also invert existing stereocenters. In addition, it is possible to separate stereoisomers once the compound has been synthesized by standard resolution techniques known to the skilled reader.

An important feature of the above-described compounds of formula I and II is their bioactivity and in particular their cytotoxic activity. In this regard, we have surprisingly found that the compounds of the present invention show an enhanced antitumor activity in comparison with those of the parent compound, Azathiocoraline, as is shown in Example 5. Hence with the present invention we provide novel pharmaceutical compositions of compounds of general formula I and II that possess cytotoxic activity, and their use as antitumor agents. Thus the present invention further provides pharmaceutical compositions comprising a compound of this invention, or a pharmaceutically acceptable salt, derivative, tautomer, prodrug or stereoisomer thereof, with a pharmaceutically acceptable carrier.

Examples of pharmaceutical compositions include any solid (tablets, pills, capsules, granules, etc.) or liquid (solutions, suspensions or emulsions) compositions, suitable formulated for oral, topical or parenteral administration.

Administration of the compounds or compositions of the present invention may be by any suitable method, such as intravenous infusion, oral preparations, and intraperitoneal and intravenous administration. We prefer that infusion times of up to 24 hours are used, more preferably 1 to 12 hours, with 1 to 6 hours being most preferred. Short infusion times which allow treatment to be carried out without an overnight stay in hospital are especially desirable. However, infusion may be 12 to 24 hours or even longer if required. Infusion may be carried out at suitable intervals of, say, 1 to 4 weeks. Pharmaceutical compositions containing a compound of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or at different time, i.e. for separate, simultaneous or sequential administration.

Antitumoral activities of the compounds of the present invention include, but are not limited, lung cancer, colon cancer, and breast cancer.

EXAMPLES

General

Protected amino acid derivatives, PyBOP, were obtained from Applied Biosystems (Framingham, Mass.), Bachem (Bubendorf, Switzerland), Albatross (Montreal, Canada), and NovaBiochem (Läufelfingen, Switzerland). 2-Chlorotrityl resin was obtained from Iris Biotech (Marktredwitz, Germany). DIEA, DIPCDI, piperidine, TFA, ammonia, iodomethane, allyl chloroformate, and p-nitrobenzyl chloroformate, were obtained from Aldrich (Milwaukee, Wis.), and EDC.HCl and HOAt were from Luxembourg Industries (Tel Aviv, Israel). DMF, $CH_2Cl_2$, Acetonitrile (HPLC grade), methanol (HPLC grade), Dioxane, $Et_2O$, TBME (t-butyl methyl ether) and EtOAc (ethyl acetate) were obtained from SDS (Peypin, France). (R)(−)-thiazolidine-4-carboxylic acid, trifluoromethanesulfonic acid, N-hydroxyacetamide methyl and N-hydroxysuccinimide were obtained from Fluka (Buchs, Switzerland). All commercial reagents and solvents were used as received with the exception of DMF and $CH_2Cl_2$, which were bubbled with nitrogen to remove volatile contaminants (DMF) and stored over activated 4 Å molecular sieves (Merck, Darmstadt, Germany), and THF which was distilled from sodium/benzophenone.

Solution reactions were performed in round-bottomed flasks. Organic solvent extracts were dried over anhydrous $MgSO_4$, followed by solvent removal under reduced pressure at temperatures below 40° C.

Solid-phase syntheses were performed in polypropylene syringes (2, 5 mL) fitted with a polyethylene porous disc. Solvents and soluble reagents were removed by suction. Removal of the Fmoc group was carried out with piperidine-DMF (1:4, v/v) (1×1 min, 2×5 min).

Washings between deprotections, coupling, and final deprotection steps were carried out with DMF (5×1 min) and $CH_2Cl_2$ (5×1 min) using 5 mL solvent·$g^{-1}$ resin for each wash. Peptide synthesis transformations and washes were performed at 25° C.

HPLC columns (Symmetry® C18 reversed-phase analytical column, 5.0 μmm×4.6 mm×150 mm and Symmetry® C18 reversed-phase semi-preparative column, 5.0 μmm×7.8 mm×100 mm) were obtained from Waters (Ireland). Analytical HPLC was carried out on a Waters instrument comprising a separation module (Waters 2695), automatic injector, photodiode array detector (Waters 996), and system controller (Millenium login). UV detection was at 220 and 254 nm, and linear gradients of $CH_3CN$ (+0.036% TFA) into $H_2O$ (+0.045% TFA), were run at 1.0 mL×$min^{-1}$ flow rate over 15 min. Semi-preparative HPLC was carried out on a Waters instrument comprising a separation module (Waters 1525 binary pump), automatic injector, and a dual absorbance detector (Waters 2487). UV detection was at 220 and 254 nm, and linear gradients of $CH_3CN$ (+0.036% TFA) into $H_2O$ (+0.045% TFA), were run at 3.0 mL×$min^{-1}$ flow rate in the conditions specified for each case.

MALDI-TOF and ES(+)-MS analyses of peptide samples were performed on an Applied Biosystems VoyagerDE RP, using ACH matrix, and in a Waters Micromass ZQ spectrometer and in an Agilent Ion Trap 1100 Series LC/MSDTrap.

Example 1

Boc-D-Dap(Me)-Gly-O-CTC-PS

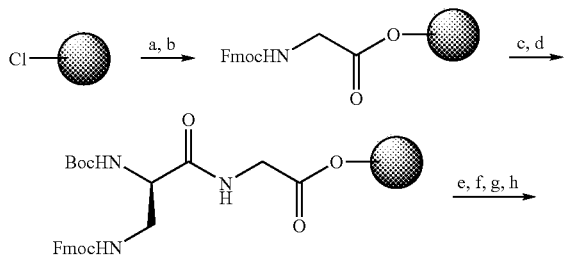

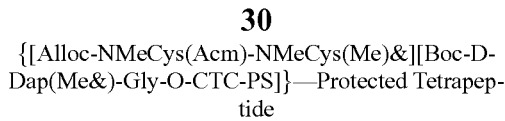

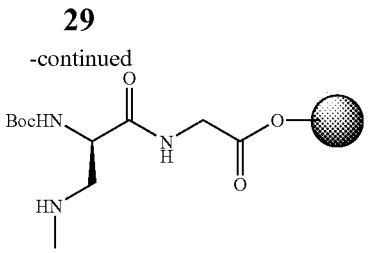

(a) CTC resin (400 mg, 1.6 mmol/g) was placed in a 10 mL polypropylene syringe fitted with 2 polyethylene filter discs. The resin was washed with DMF (5×1 min) and CH$_2$Cl$_2$ (3×1 min) and a solution of Fmoc-Gly-OH (118.8 mg, 0.4 mmol) and DIEA (474 μL, 2.66 mmol, 6.6 eq.) in CH$_2$Cl$_2$ was added. After 10 min, more DIEA (237 μL, 1.33 mmol, 3.3 eq) was added and the mixture was stirred for 50 min at room temperature.

(b) The reaction was quenched by addition of MeOH (320 μL) and the mixture stirred for further 10 min.

(c) After filtration, the peptide resin was washed with CH$_2$Cl$_2$ (3×1 min), DMF (3×1 min), piperidine-DMF (1:4; 2×1 min, 2×5 min). Loading, calculated by measuring absorbance at 290 nm, was 0.93 mmol/g.

(d) Next Boc-D-Dap(Fmoc)-OH (682 mg, 1.6 mmol, 4 eq) was introduced with HATU (456 mg, 1.6 mmol, 4 eq), HOAt (218 mg, 1.6 mmol, 4 eq) and DIEA (570 μL, 3.2 mmol, 8 eq) as coupling reagents, in DMF.

(e) After stirring for 35 min and filtration, the peptide resin was washed with DMF (3×0.5 min), CH$_2$Cl$_2$ (3×0.5 min), DMF (3×0.5 min), piperidine-DMF (1:4; 1×1 min; 3×5 min; 1×10 min), piperidine-DBU-toluene-DMF (1:1:4:14; 2×5 min) and again DMF (5×0.5 min) and CH$_2$Cl$_2$ (3×0.5 min).

(f) A solution of 2-NBS—Cl (354 mg, 1.6 mmol, 4 eq.) and DIEA (0.726 μL, 4 mmol, 10 eq) in CH$_2$Cl$_2$ was added and the mixture stirred for 90 min.

(g) After filtration and washing with CH$_2$Cl$_2$ (3×0.5 min), DMF (3×0.5 min), CH$_2$Cl$_2$ (3×0.5 min) and THF (3×0.5 min), a solution of PPh$_3$ (524 mg, 2 mmol, 5 eq) and MeOH (160 μL, 4 mmol, 10 eq) in THF and a solution of DIAD (404 μL, 2 mmol, 5 eq) in THF were mixed and added to the peptide resin. After stirring for 1 h and filtration, the peptide resin was washed with THF (3×0.5 min), CH$_2$Cl$_2$ (3×0.5 min), DMF (3×0.5 min).

An aliquot of the resin was cleavage to provide Boc-D-Dap(Me)(o-NBS)-Gly-OH:

HPLC. Conditions: $t_R$=10.0 min (gradient: 0:100 to 100:0 (ACN/H$_2$O) in 15 min); Purity 90%.

HPLC-ES. Conditions: $t_R$=10.0 min (gradient: 0:100 to 100:0 (ACN/H$_2$O) in 15 min). m/z calculated for C$_{17}$H$_{24}$N$_4$O$_9$S: 460.13. found [M+H]$^+$, 460.10.

(h) After treatments (2×15 min) with DBU (300 μL, 2 mmol, 5 eq.) and 2-mercaptoethanol (280 μL, 4 mmol, 10 eq) in DMF, the resin was washed with DMF (3×0.5 min), CH$_2$Cl$_2$ (3×0.5 min) and DMF (3×0.5 min).

An aliquot of the resin was cleavage to provide Boc-D-Dap(Me)-Gly-OH:

HPLC. Conditions: $t_R$=4.23 min (gradient: 0:100 to 100:0 (ACN/H$_2$O) in 15 min).

HPLC-ES. Conditions: $t_R$=3.87 min (gradient: 5:100 to 100:0 (ACN/H$_2$O) in 15 min). m/z calculated for C$_{11}$H$_{21}$N$_3$O$_5$: 275.15. found [M+H]$^+$, 276.73.

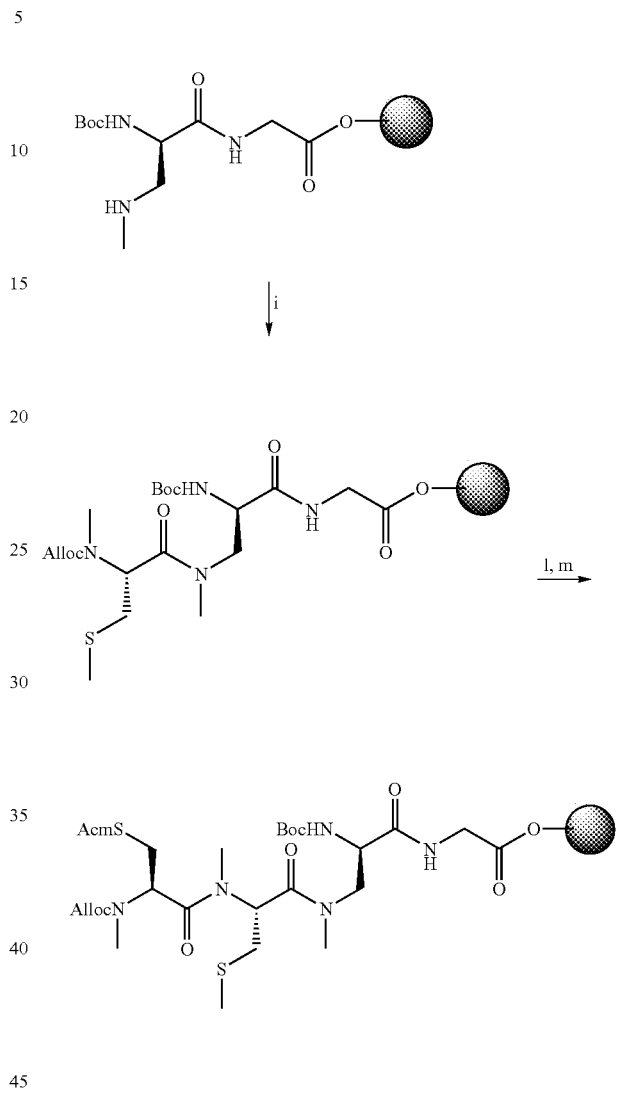

(i) The elongation of the peptide chain was performed by addition of Alloc-NMeCys(Me)-OH (373 mg 1.6 mmol, 4 eq) in the presence of HATU (456 mg, 1.6 mmol, 4 eq), HOAt (218 mg, 1.6 mmol, 4 eq) and DIEA (570 μL, 3.2 mmol, 8 eq) in DMF for 35 min and, after filtration, washings with DMF (3×0.5 min) and CH$_2$Cl$_2$ (3×0.5 min), were performed. The De Clercq test was used to indicate the completion of the couplings.

(l) Next, the peptide resin was treated (3×15 min) with Pd(PPh$_3$)$_4$ (46 mg, 0.04 mmol, 0.1 eq.) and PhSiH$_3$ (292 μL, 4 mmol, 10 eq.) in CH$_2$Cl$_2$ and washed with CH$_2$Cl$_2$ (3×0.5 min), DMF (3×0.5 min), CH$_2$Cl$_2$ (3×0.5 min), DMF (3×0.5 min).

(m) Introduction of Alloc-NMeCys(Acm)-OH (464 mg, 1.6 mmol, 4 eq) needed repetition of the coupling, in the same conditions as those provided in step (i).

The peptide resin was divided into 2 fractions: ¾ was employed in the 4+4 strategy; ¼ was reserved to dimer strategy.

Example 2

4+4 Approach

{[Boc-D-Dap(Me&¹)-Gly-NMeCys(Acm)-NMeCys(Me)&²][Alloc-NMeCys(Acm)-NMe-Cys(Me)&1][Boc-D-Dap(Me&2)-Gly-O-CTC-PS]}-Linear Protected Octapeptide The peptide resin for the 4+4 approach was further split into 2 fractions:

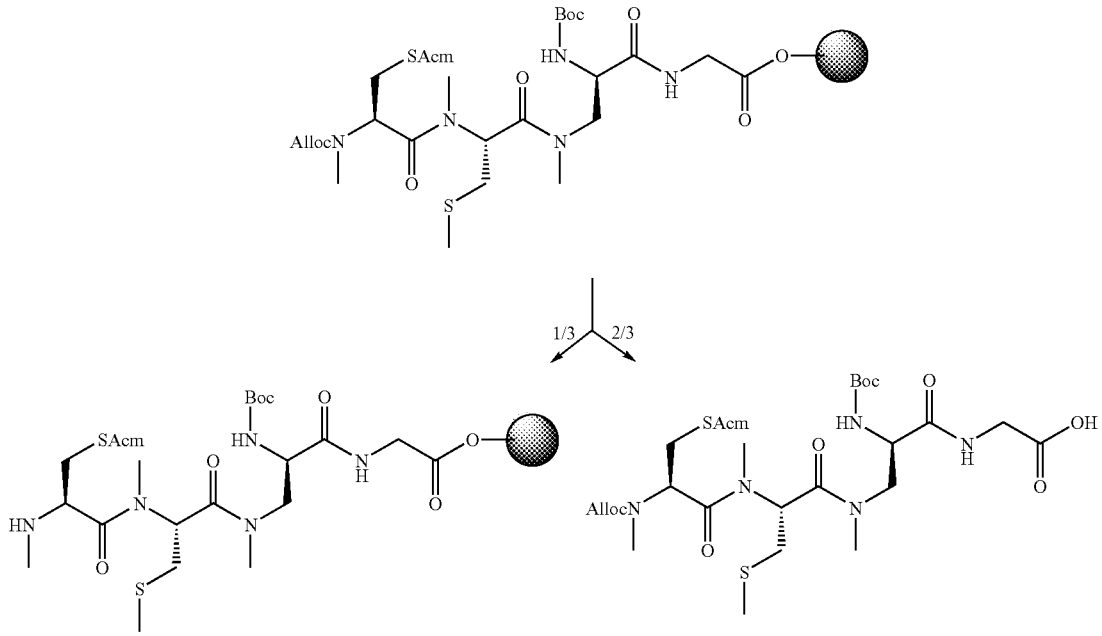

⅓ was treated with Pd(PPh$_3$)$_4$ and PhSiH$_3$ in CH$_2$Cl$_2$ as described in Example 1 (HPLC Conditions: 6.7 min (major), 6.9 min (minor); from 0:100 to 100:0 (ACN/H$_2$O));
⅔ of the resin were treated with a TFA/CH$_2$Cl$_2$ solution (2:98, 5×1 min) and the filtrates were collected in presence of H$_2$O (12 mL, 60 mL per g of resin), dried and lyophilised.

HPLC Conditions: t$_R$=9.3 min (minor), 9.7 min (major); from 0:100 to 100:0 (ACN/H$_2$O) in 15 min.
HPLC-ES Conditions: t$_R$=9.7 min; from 0:100 to 100:0 (ACN/H$_2$O) in 15 min.
m/z calculated for C$_{27}$H$_{46}$N$_6$O$_{10}$S$_2$: 678.27. found [M]$^+$, 677.91.

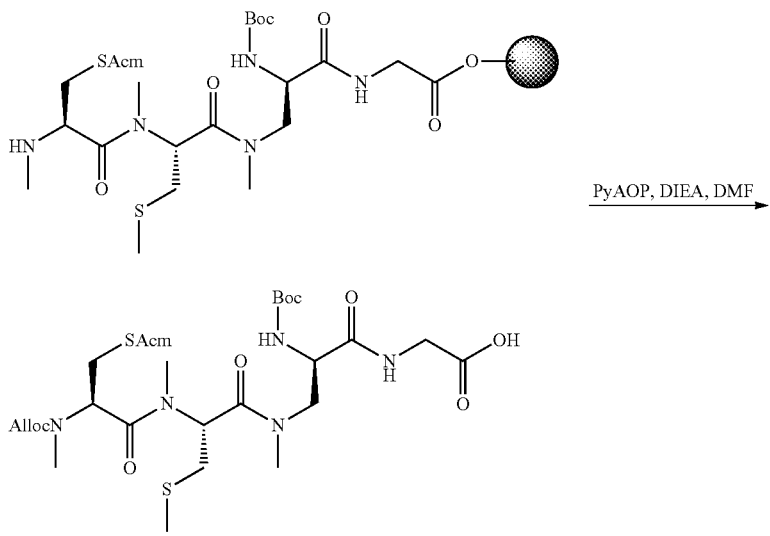

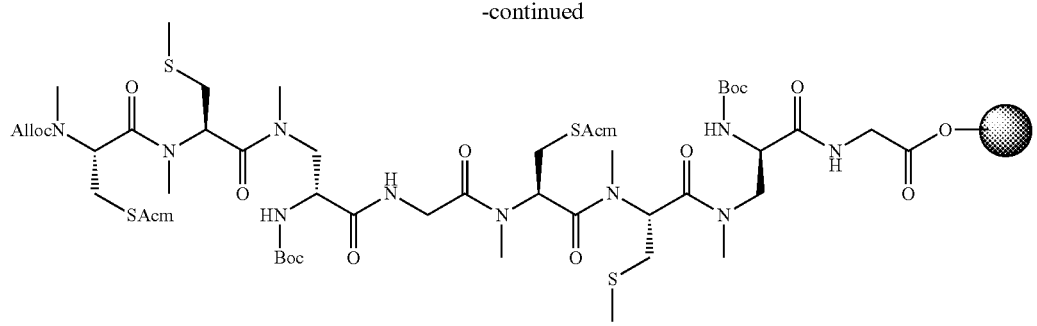

The lyophilised tetrapeptide was added to the peptide resin fraction with PyAOP (94 mg, 0.18 mmol, 2 eq calculated on loaded peptide) and DIEA (94 μL, 0.54 mmol, 6 eq) in DMF. The pH was adjusted to 8 with DIEA. The mixture was stirred overnight at room temperature. Without filtration, the De Clercq test was utilized to indicate the completion of the reaction. After a positive test, the same quantity of PyAOP and DIEA was added, and the mixture stirred further 3 hours. After a positive test, more PyAOP and DIEA were added. After 2 hours, the test revealed negative and, after filtration, the peptide resin was washed with DMF (3×0.5 min), $CH_2Cl_2$ (3×0.5 min) and DMF (3×0.5 min).

HPLC-ES Conditions: $t_R$=10.3 min; from 0:100 to 100:0 ($ACN/H_2O$) in 15 min.

m/z calculated for $C_{50}H_{86}N_{12}O_{17}S_4$: 1254.5. found $[M]^+$, 1254.32.

{[Boc-D-Dap(Me&$^1$)-Gly-NMeCys(&$^2$)—NMe-Cys(Me)&$^3$][NMeCys(&$^2$)—NMe-Cys(Me)&$^1$][Boc-D-Dap(Me&$^3$)-Gly-OH]}-Disulfide Bridge Formation The Alloc group was cleaved by treatment (3×15 min) with $Pd(PPh_3)_4$ (46 mg, 0.04 mmol, 0.1 eq.) and $PhSiH_3$ (292 μL, 4 mmol, 10 eq.) in $CH_2Cl_2$ and washed with $CH_2Cl_2$ (3×0.5 min), DMF (3×0.5 min), $CH_2Cl_2$ (3×0.5 min), and DMF (3×0.5 min). In order to make the disulfide bridge, a solution of $I_2$ (127 mg, 0.5 mmol, 5 eq, 2.5 eq×Acm) in DMF (0.01 M) was added to the peptide resin. The mixture was stirred for 10 min at room temperature and, after filtration, the treatment was repeated. Next the resin was washed with DMF (3×0.5 min), $CH_2Cl_2$ (3×0.5 min), DMF (3×0.5 min), and $CH_2Cl_2$ (3×0.5 min). HPLC-MS analysis of a cleaved peptide aliquot indicated the completion of the reaction. The peptide cleavage was achieved by treatment with a $TFA/CH_2Cl_2$ solution (2:98, 5×1 min) and the filtrates were collected in presence of $H_2O$ (6 mL, 60 mL per g of resin), dried and lyophilised.

HPLC Conditions: $t_R$=9.0; from 0:100 to 100:0 ($ACN/H_2O$) in 15 min.

HPLC-ES Conditions: $t_R$=7.5 min; from 0:100 to 100:0 ($ACN/H_2O$) in 15 min.

m/z calculated for $C_{40}H_{70}N_{10}O_{13}S_4$: 1026.40. found $[M]^+$, 1026.45.

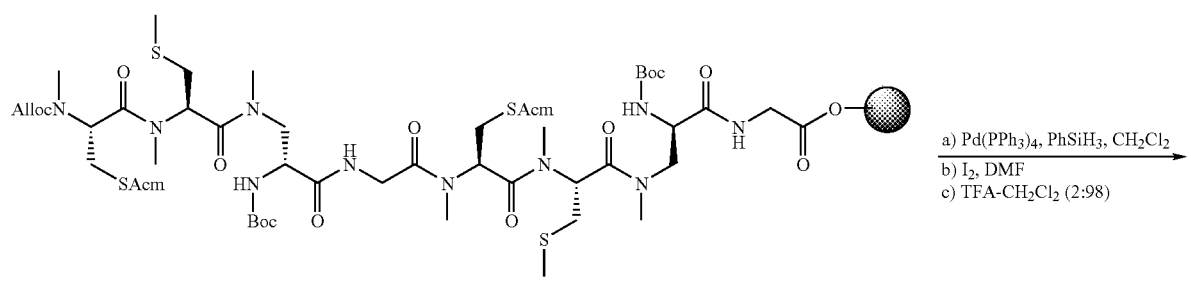

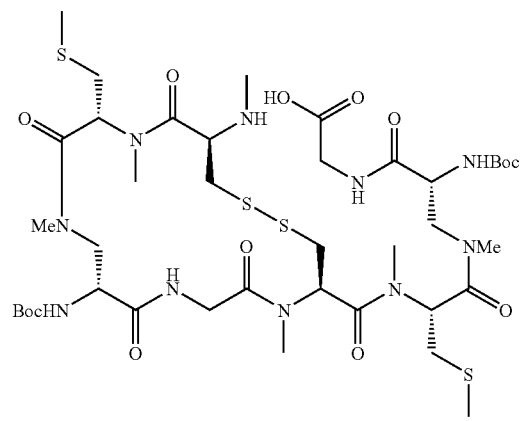

{[Boc-D-Dap(Me&¹)-Gly-NMeCys(&²)—NMe-Cys(Me)&³][Boc-D-Dap(Me&³)-Gly-NMeCys(&²)—NMe-Cys(Me)&³]—Cyclization in Solution

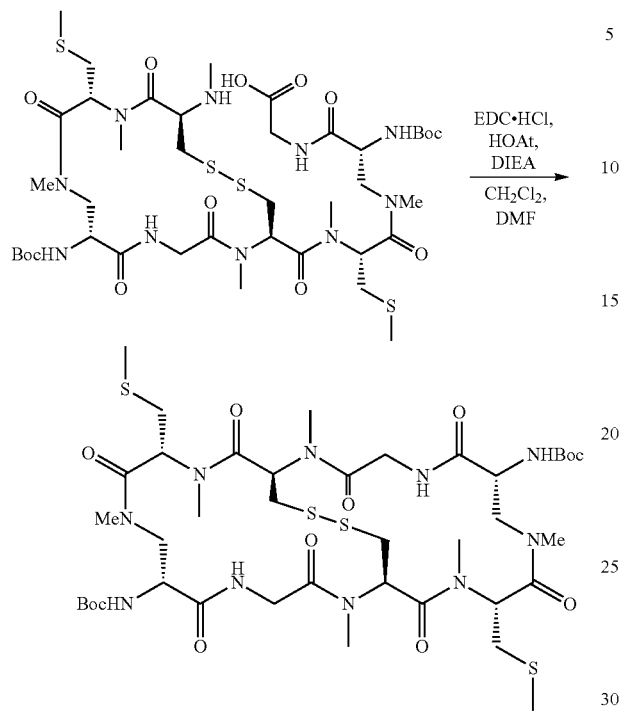

The cyclic peptide (0.1 mmol), dissolved in CH₂Cl₂/DMF (9:1, 100 mL, 1 mM) was added to a solution of HOAt (54 mg, 0.4 mmol, 4 eq.) in the minimum as possible of DMF. DIEA was added until neutral pH and when EDC.HCl (77 mg, 0.2 mmol, 2 eq.) was added, the cyclization reaction started. The mixture was stirred for 5 hours and HPLC-MS analysis indicated the completion of the reaction. The organic layer was washed with saturated aqueous solution of NH₄Cl (2×50 mL) and brine (2×50 mL), dried over MgSO₄, filtered, and evaporated under vacuum.

HPLC Conditions: $t_R$=12.3; from 0:100 to 100:0 (ACN/H₂O) in 15 min.

HPLC-ES Conditions: $t_R$=12.2 min; from 0:100 to 100:0 (ACN/H₂O) in 15 min.

m/z calculated for $C_{40}H_{68}N_{10}O_{12}S_4$: 1008.4. found [M+H− Boc]⁺ 908.49, [M+H−2 Boc]⁺ 807.45.

{[3-HQA-D-Dap(Me&¹)-Gly-NMeCys(&²)—NMe-Cys(Me)&³][3-HQA-D-Dap(Me&³)-Gly-NMeCys(&²)—NMe-Cys(Me)&¹]—Compound 2

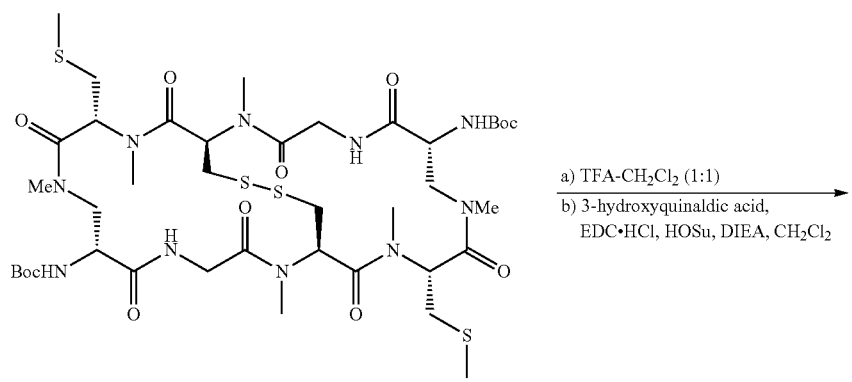

a) TFA-CH₂Cl₂ (1:1)
b) 3-hydroxyquinaldic acid, EDC·HCl, HOSu, DIEA, CH₂Cl₂

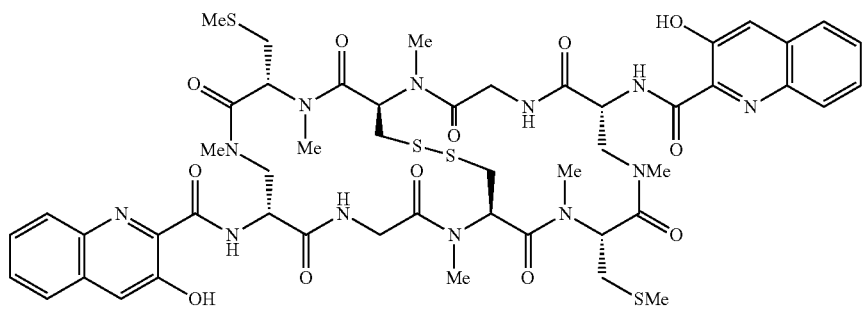

The byciclic peptide was dissolved in a TFA-CH$_2$Cl$_2$ (1:1, 2 mL) and the mixture was stirred for 1 hour at room temperature. The solvent was evaporated under reduced pressure and the residual acid was removed by coevaporations with toluene. H$_2$O was added and the product lyophilised. It was dissolved in HCl (0.001 M) and lyophilised again.

The unprotected byciclic peptide was dissolved in CH$_2$Cl$_2$ (300 µL) and DIEA until neutral pH. 3-Hydroxyquinoline-2-carboxylic acid (37 mg, 0.2 mmol, 2 eq) was preactivated with EDC.HCl (38 mg, 0.2 mmol, 2 eq) and HOSu (22 mg, 0.2 mmol, 2 eq) in CH$_2$Cl$_2$ (1 mL) and, after 15 min, this solution was added to the previously prepared peptide solution. The mixture was stirred for 20 h and HPLC-MS analysis indicated completion of the reaction. The organic layer was washed with saturated aqueous solution of NH$_4$Cl (2×50 mL) and brine (2×50 mL), dried over MgSO$_4$, filtered, and evaporated under vacuum.

HPLC Conditions: $t_R$=13.2; from 0:100 to 100:0 (ACN/H$_2$O) in 15 min.

HPLC-ES Conditions: $t_R$=13.3 min; from 0:100 to 100:0 (ACN/H$_2$O) in 15 min. m/z calculated for C$_{50}$H$_{62}$N$_{12}$O$_{12}$S$_4$: 1150.4. found [M+H+] 1151.5.

Example 3

Dimer Strategy

{[NMeCys($\&^1$)-NMeCys(Me)$\&^2$)][Boc-D-Dap(Me$\&^2$)-Gly-OH]}$_2$-Dimer

The peptide resin was treated with Pd(PPh$_3$)$_4$ and PhSiH$_3$ in CH$_2$Cl$_2$ as described in Example 1. The dimer formation was achieved by treatments (2×10 min) with a solution of I$_2$ (126.9 mg, 0.5 mmol, 0.5 eq.) in DMF (10 mL), followed by washing with DMF (3×0.5 min), CH$_2$Cl$_2$ (3×0.5 min), DMF (3×0.5 min), and CH$_2$Cl$_2$ (3×0.5 min). HPLC-MS analysis of a cleaved peptide aliquot indicated the completion of the reaction. Next the peptide was cleaved from the resin by treatment with a TFA/CH$_2$Cl$_2$ solution (2:98, 5×1 min) and the filtrates were collected in presence of H$_2$O (6 mL, 60 mL per g of resin), dried and lyophilised.

HPLC. Conditions: $t_R$=7.1; from 0:100 to 100:0 (ACN/H$_2$O) in 15 min.

HPLC-ES. Conditions: $t_R$=6.1 min; from 0:100 to 100:0 (ACN/H$_2$O) in 15 min.

m/z calculated for C$_{40}$H$_{72}$N$_{10}$O$_{12}$S$_4$: 1044.4. found [M+H]$^+$ 1043.49, [M+H]$^{+2}$ 522.49.

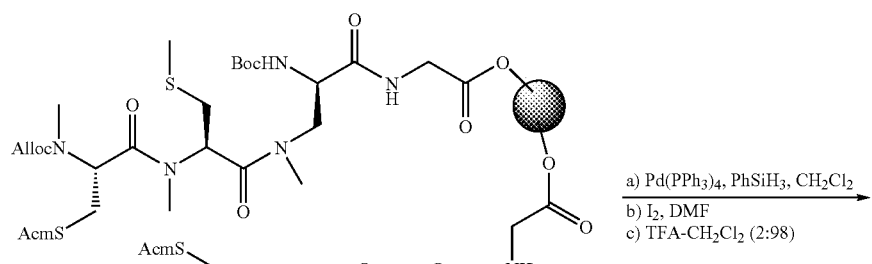

a) Pd(PPh$_3$)$_4$, PhSiH$_3$, CH$_2$Cl$_2$
b) I$_2$, DMF
c) TFA-CH$_2$Cl$_2$ (2:98)

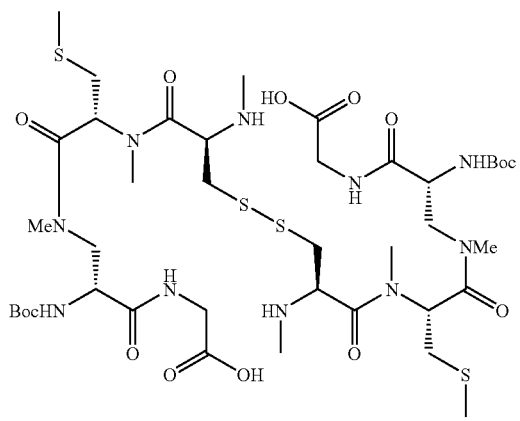

{[Boc-D-Dap(Me&¹)-Gly-NMeCys(&²)—NMe-Cys(Me)&³][Boc-D-Dap(Me&³)-Gly-NMeCys(&²)—NMe-Cys(Me)&¹]—Cyclization Reaction

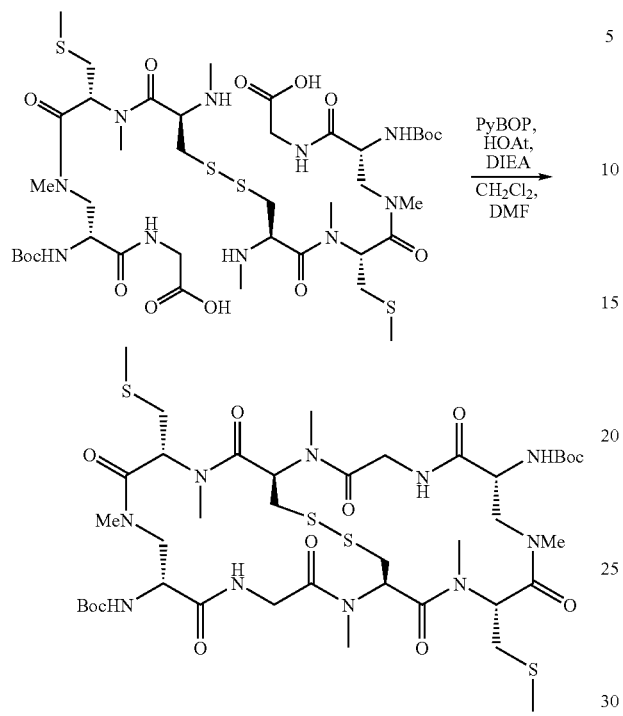

The peptide (0.05 mmol) was dissolved in CH₂Cl₂/DMF (9:1) and added to a solution of HOAt (54 mg, 0.4 mmol, 8 eq.) in CH₂Cl₂/DMF (9:1, 50 mL, 1 mM). The addition of DIEA until pH 8 and PyBOP (208 mg, 0.4 mmol, 8 eq) started the reaction. The mixture was stirred for 12 hours and HPLC-MS analysis indicated the completion of the reaction. The organic layer was washed with saturated NH₄Cl (2×50 mL) and brine (2×50 mL), dried with MgSO₄ and evaporated under vacuum.

HPLC Conditions: $t_R$=12.1; from 0:100 to 100:0 (ACN/H₂O) in 15 min.

HPLC-ES Conditions: $t_R$=12.1 min; from 0:100 to 100:0 (ACN/H₂O) in 15 min.

m/z calculated for $C_{40}H_{68}N_{10}O_{12}S_4$: 1008.40. found [M]⁺ 1008.89.

{[3-HQA-D-Dap(Me&¹)-Gly-NMeCys(&²)—NMe-Cys(Me)&³][3-HQA-D-Dap(Me&³)-Gly-NMeCys(&²)—NMe-Cys(Me)&¹]—Compound 2

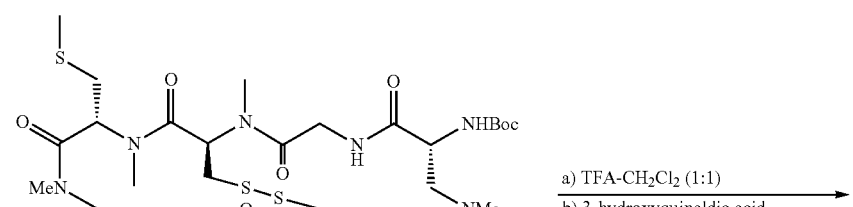

a) TFA-CH₂Cl₂ (1:1)
b) 3-hydroxyquinaldic acid, EDC·HCl, HOSu, DIEA, CH₂Cl₂

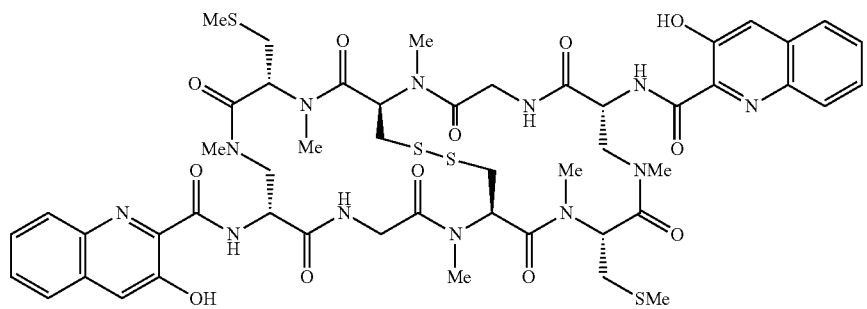

Compound 2 was obtained following the same procedure disclosed in the last step of example 2.

HPLC Conditions: $t_R$=13.2; from 0:100 to 100:0 (ACN/H$_2$O) in 15 min.

HPLC-ES Conditions: $t_R$=13.3 min; from 0:100 to 100:0 (ACN/H$_2$O) in 15 min.

m/z calculated for $C_{50}H_{62}N_{12}O_{12}S_4$: 1150.40. found [M+H]$^+$ 1151.53.

Example 4

Purification and Characterization of Compound 2

The crude of compound 2 obtained in example 2 and 3 were purified by HPLC to afford purified compound 2 (952 μg, 1.0% yield).

HPLC Conditions of purification: linear gradient from 45:55 to 60:40 (ACN/H$_2$O) in 30 min; flow rate 3 mL/min.

$t_R$=13.6 min (4+4 strategy)
$t_R$=13.0 min (dimer strategy)

Analytical HPLC Conditions: $t_R$=13.0; from 5:95 to 100:0 (ACN/H$_2$O) in 15 min.

MALDI-TOF: m/z calculated for $C_{50}H_{62}N_{12}O_{12}S_4$: 1150.4. found [M+H]$^+$ 1151.5; [M+Na]$^+$ 1173.8

HRMS calculated for $C_{50}H_{63}N_{12}O_{12}S_4$: 1151.3566. found 1151.3573

Example 5

Bioassays for the Detection of Antitumor Activity

The aim of this assay is to evaluate the in vitro cytostatic (ability to delay or arrest tumor cell growth) or cytotoxic (ability to kill tumor cells) activity of the samples being tested.

Cell Lines

| Name | N° ATCC | Species | Tissue | Characteristics |
|---|---|---|---|---|
| A549 | CCL-185 | human | lung | lung carcinoma (NSCLC) |
| HT29 | HTB-38 | human | colon | colorectal adenocarcinoma |
| MDA-MB-231 | HTB-26 | human | breast | breast adenocarcinoma |

Evaluation of Cytotoxic Activity Using the SBR Colorimetric Assay

A colorimetric type of assay, using sulforhodamine B (SRB) reaction has been adapted for a quantitative measurement of cell growth and viability (following the technique described by Skehan P et al. J. Natl. Cancer Inst. 1990, 82, 1107-1112).

This form of assay employs SBS-standard 96-well cell culture microplates (Faircloth et al. Methods in cell science, 1988, 11(4), 201-205; Mosmann et al. Journal of. Immunological. Methods, 1983, 65(1-2), 55-63). All the cell lines used in this study, derived from different types of human cancer, were obtained from the American Type Culture Collection (ATCC).

Cells were maintained in Dulbecco's Modified Eagle Medium (DMEM) supplemented with 10% Fetal Bovine Serum (FBS), 2 mM L-glutamine, 100 U/mL penicillin and 100 U/mL streptomycin at 37° C., 5% CO$_2$ and 98% humidity. For the experiments, cells were harvested from subconfluent cultures using trypsinization and resuspended in fresh medium before counting and plating.

Cells were seeded in 96 well microtiter plates at 5×10$^3$ cells per well in aliquots of 150 μL, and allowed to attach to the plate surface for 18 hours in drug free medium. One control (untreated) plate of each cell line was fixed (as described below) and used for time zero reference value. Afterwards, test samples were added to the cultures in ten serial dilutions, in aliquots of 50 μL, ranging from 10 to 0.00262 μg/mL. After 48 hours exposure, the antitumor effect was estimated by the SRB method: Briefly, cells were washed twice with PBS, fixed for 15 min in 1% glutaraldehyde solution, rinsed twice in PBS, and stained in 0.4% SRB solution for 30 min at room temperature. Cells were then rinsed several times with 1% acetic acid solution and air-dried. SRB was then extracted in 10 mM trizma base solution and the absorbance measured in an automated spectrophotometric plate reader at 490 nm. Cell survival was expressed as percentage of control cell growth. The final effect of the sample being tested was estimated by applying the NCI algorithm (Boyd M R and Paull K D. Drug Dev. Res. 1995, 34, 91-104).

Using the mean±SD of triplicate cultures, a dose-response curve was automatically generated using nonlinear regression analysis. Three reference parameters were calculated (NCI algorithm) by automatic interpolation: $GI_{50}$=concentration that produces 50% growth inhibition; TGI=total growth inhibition (cytostatic effect) and $LC_{50}$=concentration that produces 50% net cell killing (cytotoxic effect).

Table 1 illustrate data on the biological activity of compounds of the present invention in comparison with those of the parent compound, Azathiocoraline, that was obtained following the procedure disclosed in Bayó-Puxan, Núria: Ph. D. Thesis, University of Barcelona, 2006.

TABLE 1

Cytotoxicity assay - Activity Data (Molar)

| | | Azathiocoraline | Compound 2 |
|---|---|---|---|
| MDA-MB-231 | $GI_{50}$ | 2.14E−06 | 4.08E−09 |
| | TGI | >8.90E−06 | 4.26E−08 |
| | $LC_{50}$ | >8.90E−06 | 3.73E−07 |
| HT29 | $GI_{50}$ | 3.12E−06 | 2.08E−08 |
| | TGI | >8.90E−06 | 1.13E−07 |
| | $LC_{50}$ | >8.90E−06 | 7.47E−07 |
| A549 | $GI_{50}$ | 3.74E−06 | 3.39E−09 |
| | TGI | >8.90E−06 | 2.00E−08 |
| | $LC_{50}$ | >8.90E−06 | 1.65E−07 |

The invention claimed is:

1. A compound of formula I

Formula I wherein $R_1$, $R_4$, $R_6$, and $R_9$ are each independently selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl;

$R_3$ and $R_8$ are each independently a substituted or unsubstituted $C_1$-$C_{12}$ mercaptoalkyl group wherein the mercapto group may be optionally protected; or $R_3$ with $R_8$ form a group —CH$_2$—S—S—CH$_2$—;

$R_2$ is hydrogen;

R$_7$ is hydrogen; or the pair R$_1$-R$_2$ and/or R$_6$-R$_7$ independently form a substituted or unsubstituted C$_1$-C$_{12}$ alkylidene or together with the corresponding C atom to which they are attached form a substituted or unsubstituted C$_3$-C$_{12}$ cycloalkyl;

R$_5$ and R$_{10}$ are each independently selected from amino protecting group and —(C═O)R″ wherein each R″ is independently selected from substituted or unsubstituted heterocyclic group and substituted or unsubstituted heterocyclyalkyl group;

R$_a$, R$_b$, R$_c$, R$_d$, R$_e$, and R$_f$ are each independently selected from hydrogen and substituted or unsubstituted C$_1$-C$_{12}$ alkyl;

Y is selected from S, O, and NR$_i$;

R$_h$ is selected from substituted or unsubstituted C$_1$-C$_{12}$ alkyl, a —(CH$_2$—CH$_2$O)$_n$—CH$_3$ group wherein a is from 1 to 25, substituted or unsubstituted C$_2$-C$_{12}$ alkenyl and substituted or unsubstituted C$_2$-C$_{12}$ alkynyl; and R$_i$ is a group selected from hydrogen, substituted of unsubstituted C$_1$-C$_{12}$ alkyl, a —(CH$_2$—CH$_2$O)$_n$—CH$_3$ group wherein n is from 1 to 25, substituted or unsubstituted C$_2$-C$_{12}$ alkenyl and substituted or unsubstituted C$_2$-C$_{12}$ alkynyl;

or a pharmaceutically acceptable salt, tautomer, ester or stereoisomer thereof.

2. The compound according to claim 1, wherein R$_4$ and R$_9$ are each independently selected from hydrogen and substituted or unsubstituted C$_1$-C$_{12}$ alkyl.

3. The compound according to claim 2, wherein R$_4$ and R$_9$ are each independently selected from hydrogen and substituted or unsubstituted alkyl group selected from methyl, ethyl, propyl, isopropyl, butyl, isobutyl, sec-butyl and tert-butyl.

4. The compound according to claim 1, wherein R$_3$ and R$_8$ form a group —CH$_2$—S—S—CH$_2$—.

5. The compound according to claim 1, wherein R$_2$ and R$_7$ are hydrogen.

6. The compound according to claim 1, wherein R$_a$, R$_b$, R$_c$, R$_d$, R$_e$, and R$_f$ are each independently selected from hydrogen or substituted or unsubstituted C$_1$-C$_6$ alkyl.

7. The compound according to claim 1, having the following formula II

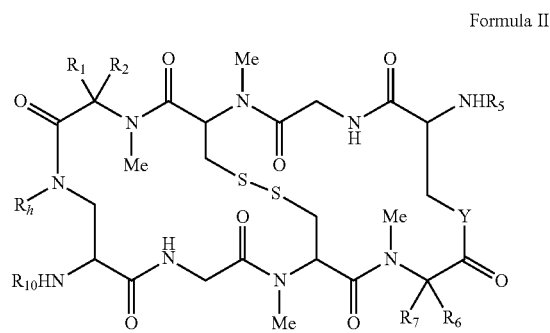

Formula II or a pharmaceutically acceptable salt, tautomer, ester or stereoisomer thereof.

8. The compound according to claim 7, wherein R$_1$ and R$_6$ are each independently selected from hydrogen and substituted or unsubstituted C$_1$-C$_{12}$ alkyl.

9. The compound according to claim 8, wherein R$_1$ and R$_6$ are each independently selected from methyl, methylthiomethyl and isopropyl.

10. The compound according to claim R$_2$ and R$_7$ are hydrogen.

11. The compound according to claim 7, wherein R$_5$ and R$_{10}$ are each independently selected from amino protecting group and —(C═O)R″, wherein each R″ is a substituted or unsubstituted heteroaromatic group.

12. The compound according to claim 11, wherein R$_5$ and R$_{10}$ are each independently —(C═O)R″ wherein each R″ is a substituted or unsubstituted quinolyl group.

13. The compound according to claim 7, wherein R$_h$ is a C$_1$-C$_{12}$ alkyl or a —(CH$_2$—CH$_2$O)$_n$—CH$_3$ group wherein n is from 1 to 25.

14. The compound according to claim 13, wherein R$_h$ is selected from methyl, ethyl, propyl and isopropyl.

15. The compound according to claim 7, wherein Y is S or NR$_i$, and R$_i$ is hydrogen, substituted or unsubstituted C$_1$-C$_{12}$ alkyl or a —(CH$_2$—CH$_2$O)$_n$—CH$_3$ group wherein n is from 1 to 25.

16. The compound according to claim 15, wherein Y is NR$_i$, and R$_i$ is selected from methyl, ethyl, propyl, and isopropyl.

17. The compound according to claim 1, having the following formula

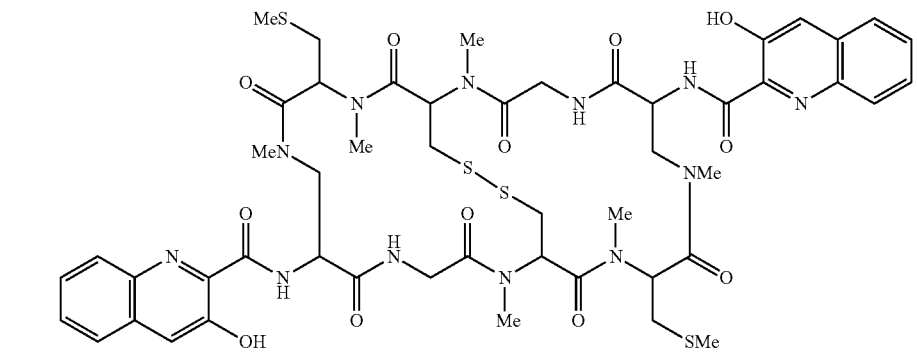 [SMILES: CSCC1C(=O)N(C)CC(NC(=O)c2nc3ccccc3cc2O)C(=O)NCC(=O)N(C)C2CSSCC(C(=O)N1C)N(C)C(=O)CNC(=O)C(NC(=O)c1nc3ccccc3cc1O)CN(C)C(=O)C(CSC)N(C)C2=O]

or a pharmaceutically acceptable salt, tautomer, ester or stereoisomer thereof.

18. The compound according to claim 17, having the following formula

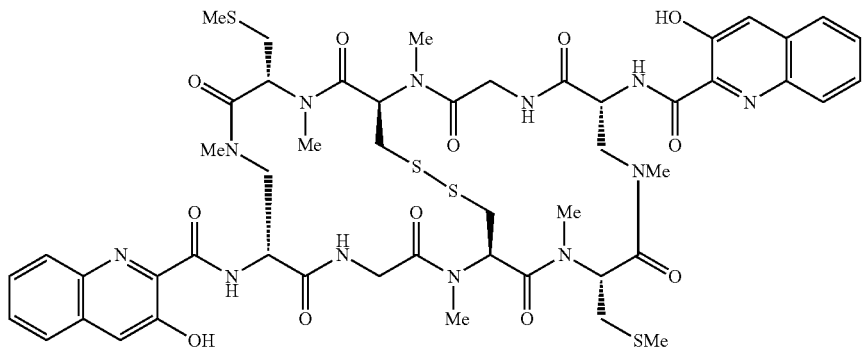 [SMILES: CSC[C@H]1C(=O)N(C)C[C@@H](NC(=O)c2nc3ccccc3cc2O)C(=O)NCC(=O)N(C)[C@H]2CSSC[C@@H](C(=O)N1C)N(C)C(=O)CNC(=O)[C@H](NC(=O)c1nc3ccccc3cc1O)CN(C)C(=O)[C@H](CSC)N(C)C2=O]

or a pharmaceutically acceptable salt, tautomer, or ester thereof.

19. A pharmaceutical composition comprising a compound according to formula I

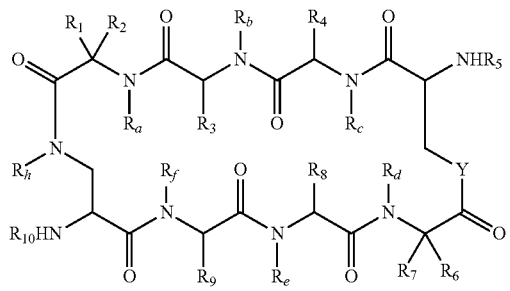

wherein
- $R_1$, $R_4$, $R_6$, and $R_9$ are each independently selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl;
- $R_3$ and $R_8$ are each independently a substituted or unsubstituted $C_1$-$C_{12}$ mercaptoalkyl group wherein the mercapto group may be optionally protected; or $R_3$ with $R_8$ form a group —$CH_2$—S—S—$CH_2$—;
- $R_2$ is hydrogen;
- $R_7$ is hydrogen; or
- the pair $R_1$-$R_2$ and/or $R_6$-$R_7$ independently form a substituted or unsubstituted $C_1$-$C_{12}$ alkylidene or together with the corresponding C atom to Which they are attached form a substituted or unsubstituted $C_3$-$C_{12}$ cycloalkyl;
- $R_5$ and $R_{10}$ are each independently selected from amino protecting group and —(C═O)R" wherein each R" is independently selected from substituted or unsubstituted heterocyclic group and substituted or unsubstituted heterocyclylalkyl group;
- $R_a$, $R_b$, $R_c$, $R_d$, $R_e$, and $R_f$ are each independently selected from hydrogen and substituted or unsubstituted $C_1$-$C_{12}$ alkyl;
- Y is selected from S, O, and $NR_i$;
- $R_h$ is selected from substituted or unsubstituted $C_1$-$C_{12}$ alkyl, a —($CH_2$—$CH_2O$)$_n$—$CH_3$ group wherein n is from 1 to 25, substituted or unsubstituted alkenyl and substituted or unsubstituted $C_2$-$C_{12}$ alkynyl; and
- $R_i$ is a group selected from hydrogen, substituted of unsubstituted $C_1$-$C_{12}$ alkyl, a —($CH_2$—$CH_2O$)$_n$—$CH_3$ group wherein n from 1 to 25, substituted or unsubstituted $C_1$-$C_{12}$ alkenyl and substituted or unsubstituted $C_2$-$C_{12}$ alkynyl, or a pharmaceutically acceptable salt, tautomer, ester or stereoisomer thereof, and a pharmaceutically acceptable diluent or carrier.

20. A method of treating a mammal affected by cancer which comprises administering to the affected mammal a therapeutically effective amount of a compound according to formula I

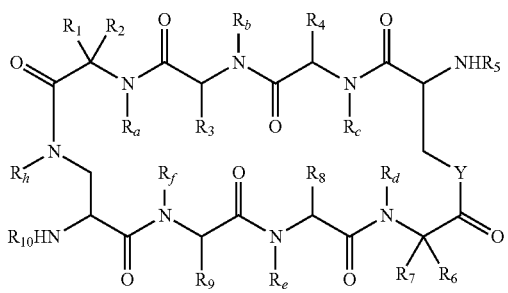

wherein
- $R_1$, $R_4$, $R_6$, and $R_9$ are each independently selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl;
- $R_3$ and $R_8$ are each independently a substituted or unsubstituted $C_1$-$C_{12}$ mercaptoalkyl group wherein the mercapto group may be optionally protected; or $R_3$ with $R_8$ form a group —$CH_2$—S—S—$CH_2$—;
- $R_2$ is hydrogen;
- $R_7$ is hydrogen; or
- the pair $R_1$-$R_2$ and/or $R_6$-$R_7$ independently form a substituted or unsubstituted $C_1$-$C_{12}$ alkylidene or together with the corresponding C atom to which they are attached form a substituted or unsubstituted $C_3$-$C_{12}$ cycloalkyl;
- $R_5$ and $R_{10}$ are each independently selected from amino protecting group and —(C═O)R" wherein each R" is independently selected from substituted or unsubstituted heterocyclic group and substituted or unsubstituted heterocyclylalkyl group;
- $R_a$, $R_b$, $R_c$, $R_d$, $R_e$, and $R_f$ are each independently selected from hydrogen and substituted or unsubstituted $C_1$-$C_{12}$ alkyl;
- is selected from S, O and $NR_i$;

$R_n$ is selected from substituted or unsubstituted $C_1$-$C_{12}$ alkyl, a —$(CH_2$—$CH_2O)_n$—$CH_3$ group wherein n is from 1 to 25, substituted or unsubstituted alkenyl and substituted or unsubstituted $C_2$-$C_{12}$ alkynyl; and $R_i$ is a group selected from hydrogen, substituted of unsubstituted $C_1$-$C_{12}$ alkyl, a —$(CH_2$—$CH_2O)_n$—$CH_3$ group wherein n is from 1 to 25, substituted or unsubstituted $C_2$-$C_{12}$ and substituted or unsubstituted $C_2$-$C_{12}$ alkynyl or a pharmaceutically acceptable salt, tautomer ester or stereoisomer thereof, wherein the cancer is selected from lung cancer, colon cancer and breast cancer.

21. A method of treating a mammal affected by cancer which comprises administering to the affected mammal a therapeutically effective amount of a compound having the following formula

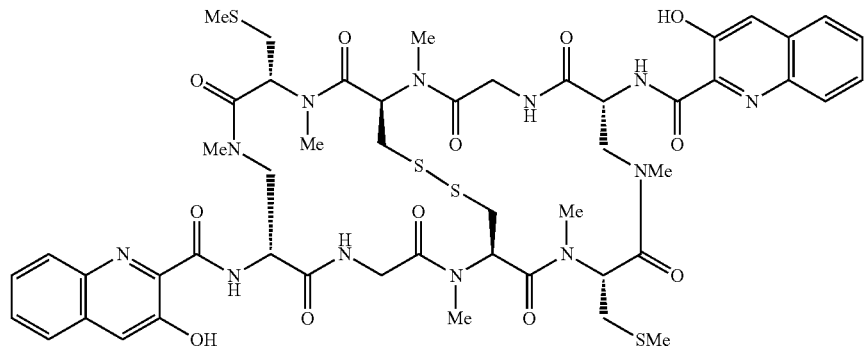 [SMILES: CSC[C@H]1C(=O)N(C)C[C@@H](NC(=O)c2nc3ccccc3cc2O)C(=O)NCC(=O)N(C)[C@H]2CSSC[C@@H](C(=O)N1C)N(C)C(=O)CNC(=O)[C@H](NC(=O)c1nc3ccccc3cc1O)CN(C)C(=O)[C@H](CSC)N(C)C2=O]

or a pharmaceutically acceptable salt, tautomer or ester thereof, wherein the cancer is selected from lung cancer, colon cancer and breast cancer.

22. The method according to claim 20, wherein the mammal is human.

23. The method according to claim 21, i herein the mammal is human.

* * * * *

UNITED STATES PATENT AND TRADEMARK OFFICE
CERTIFICATE OF CORRECTION

Page 1 of 1

PATENT NO. : 8,748,388 B2
APPLICATION NO. : 12/746957
DATED : June 10, 2014
INVENTOR(S) : Judit Tulla-Puche et al.

It is certified that error appears in the above-identified patent and that said Letters Patent is hereby corrected as shown below:

In the Claims:

Column 43, claim 1, lines 18-19, the term "$R_b$ is selected from substituted or unsubstituted $C_1$-$C_{12}$ alkyl, a –$(CH_2$-$CH_2O)_n$-$CH_3$ group wherein a is…" should read --$R_h$ is selected from substituted or unsubstituted $C_1$-$C_{12}$ alkyl a –$(CH_2$-$CH_2O)_n$-$CH_3$ group wherein n is…--.

Column 45, claim 19, line 64, the term "from 1 to 25, substituted or unsubstituted alkenyl and" should read --from 1 to 25, substituted or unsubstituted $C_2$-$C_{12}$ alkenyl and--.

Column 46, claim 20, line 67, the term "is selected from S, O and $NR_i$" should read --Y is selected from S, O and $NR_i$--.

Column 47, claim 20, line 3, the term "from 1 to 25, substituted or unsubstituted alkenyl and" should read --from 1 to 25, substituted or unsubstituted $C_2$-$C_{12}$ alkenyl and--.

Column 47, claim 20, lines 7-8, the term "wherein n is from 1 to 25, substituted or unsubstituted $C_2$-$C_{12}$ and substituted or unsubstituted $C_2$-$C_{12}$ alkynyl" should read --wherein n is from 1 to 25, substituted or unsubstituted $C_2$-$C_{12}$ alkenyl and substituted or unsubstituted $C_2$-$C_{12}$ alkynyl--.

Column 48, claim 23, line 30, the term "… i herein the mammal" should read --wherein the mammal--.

Signed and Sealed this
First Day of March, 2016

Michelle K. Lee
*Director of the United States Patent and Trademark Office*